(12) United States Patent
Hickey et al.

(10) Patent No.: US 9,006,396 B2
(45) Date of Patent: Apr. 14, 2015

(54) CSPCNA ISOFORM ANTIBODIES AND USES THEREOF

(75) Inventors: Robert J. Hickey, Lakeview Terrace, CA (US); Linda H. Malkas, Lakeview Terrace, CA (US); Lauren Schnaper, Lutherville, MD (US)

(73) Assignees: Linda H. Malkas, Lakeview Terrace, CA (US); Robert J. Hickey, Lakeview Terrace, CA (US)

( * ) Notice: Subject to any disclaimer, the term of this patent is extended or adjusted under 35 U.S.C. 154(b) by 0 days.

(21) Appl. No.: 13/477,419

(22) Filed: May 22, 2012

(65) Prior Publication Data
US 2012/0244076 A1 Sep. 27, 2012

Related U.S. Application Data

(63) Continuation of application No. 11/912,704, filed as application No. PCT/US2006/016096 on Apr. 27, 2006, now abandoned.

(60) Provisional application No. 60/689,614, filed on Jun. 9, 2005, provisional application No. 60/675,275, filed on Apr. 27, 2005.

(51) Int. Cl.
*C07K 16/00* (2006.01)
*C07K 16/30* (2006.01)
*C07K 16/44* (2006.01)

(52) U.S. Cl.
CPC ............ *C07K 16/3015* (2013.01); *C07K 16/44* (2013.01); *C07K 2316/96* (2013.01); *C07K 2317/73* (2013.01)

(58) Field of Classification Search
None
See application file for complete search history.

(56) References Cited

PUBLICATIONS

Roos et al, Exp Cell Res, 1996, 226:208-213.*
Hudson et al, J Immunol Methods, 1999, 231:177-189.*

* cited by examiner

*Primary Examiner* — Mark Halvorson
(74) *Attorney, Agent, or Firm* — Whiteford, Taylor & Preston, LLP; Joseph L. Morales

(57) ABSTRACT

Antibodies specifically bind only to a cancer specific proliferating cell nuclear antigen (csPCNA) isoform and not to the non-malignant proliferating cell nuclear antigen (nmPCNA) isoform. Methods and compositions to detect the presence of csPCNA isoform are disclosed.

41 Claims, 11 Drawing Sheets

SEQ ID NO.: 3

```
  1  MetPheGluAlaArgLeuValGlnGlySer  IleLeuLysLysValLeuGluAlaLeuLys
     AspLeuIleAsnGluAlaCysTrpAspIle  SerSerSerGlyValAsnLeuGlnSerMet
     AspSerSerHisValSerLeuValGlnLeu  ThrLeuArgSerGluGlyPheAspThrTyr

61  ArgCysAspArgAsnLeuAlaMetGlyVal  AsnLeuThrSerMetSerLysIleLeuLys
     CysAlaGlyAsnGluAspIleIleThrLeu  ArgAlaGluAspAsnAlaAspThrLeuAla
     LeuValPheGluAlaProAsnGlnGluLys  ValSerAspTyrGluMetLysLeuMetAsp

121  LeuAspValGluGlnLeuGlyIleProGlu  GlnGluTyrSerCysValValLysMetPro
     SerGlyGluPheAlaArgIleCysArgAsp  LeuSerHisIleGlyAspAlaValValIle
     SerCysAlaLysAspGlyValLysPheSer  AlaSerGlyGluLeuGlyAsnGlyAsnIle

181  LysLeuSerGlnThrSerAsnValAspLys  GluGluGluAlaValThrIleGluMetAsn
     GluProValGlnLeuThrPheAlaLeuArg  TyrLeuAsnPhePheThrLysAlaThrPro
     LeuSerSerThrValThrLeuSerMetSer  AlaAspValProLeuValValGluTyrLys

241  IleAlaAspMetGlyHisLeuLysTyrTyr  LeuAlaProLysIleGluAspGluGluGly Ser
```

SEQ ID NO.: 1
      LeuGlyIleProGluGlnGluTyr

SEQ ID NO.: 2
    CysGlyGlyGlyLeuGlyIleProGluGlnGluTyr

SEQ ID NO.: 4
    CysAspValGluGlnLeuGlyIleProGluGlnGluTyr

FIG. 1

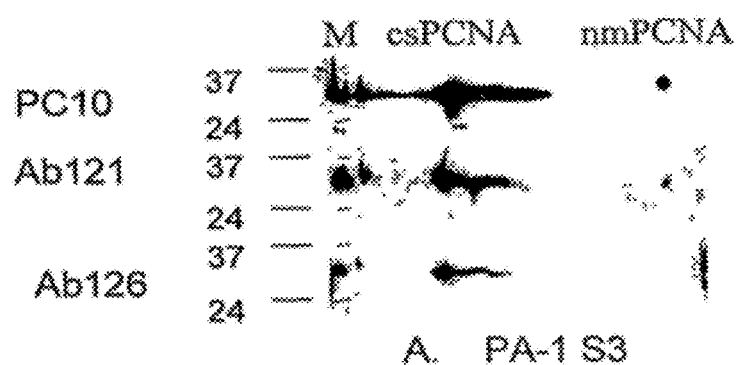
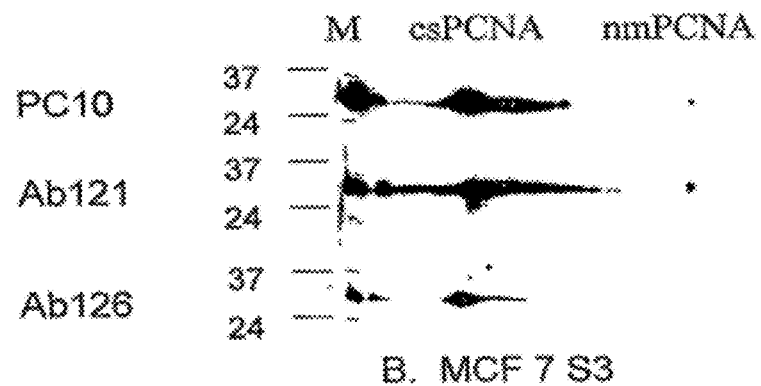
FIG. 2

(A)
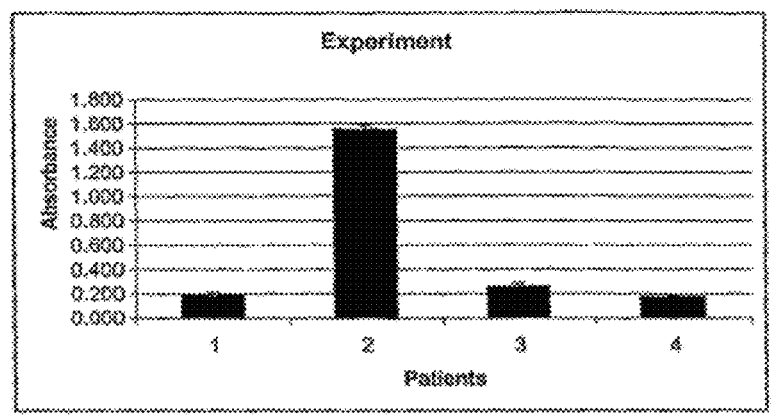
(B)
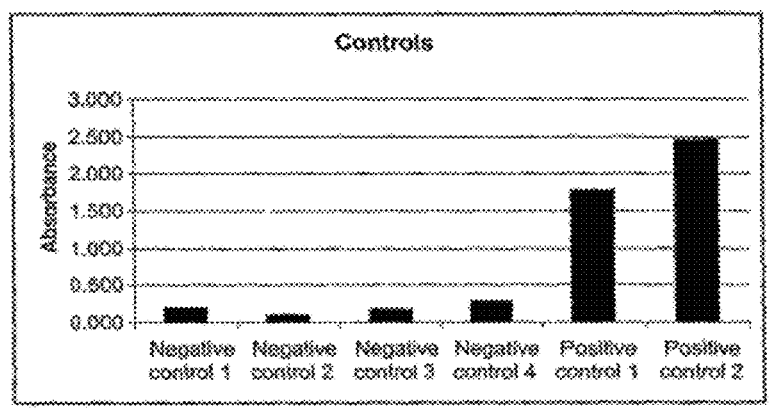
(C)
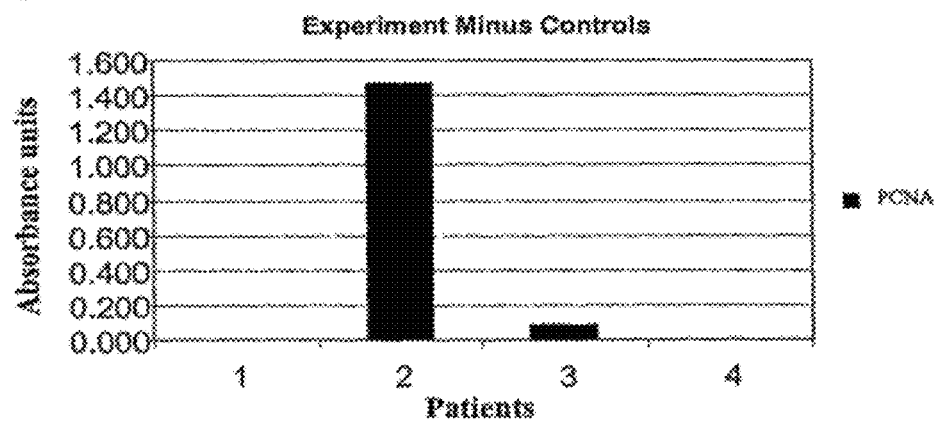
FIG. 14

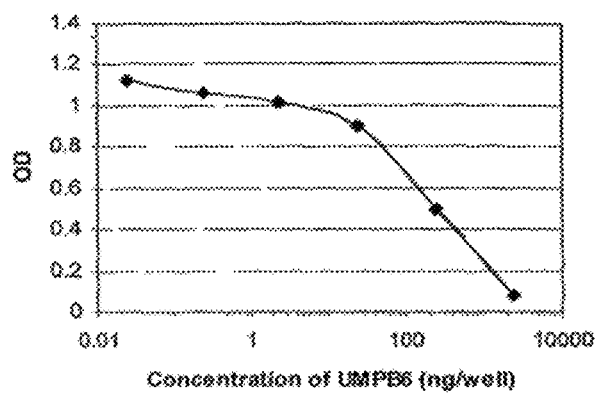
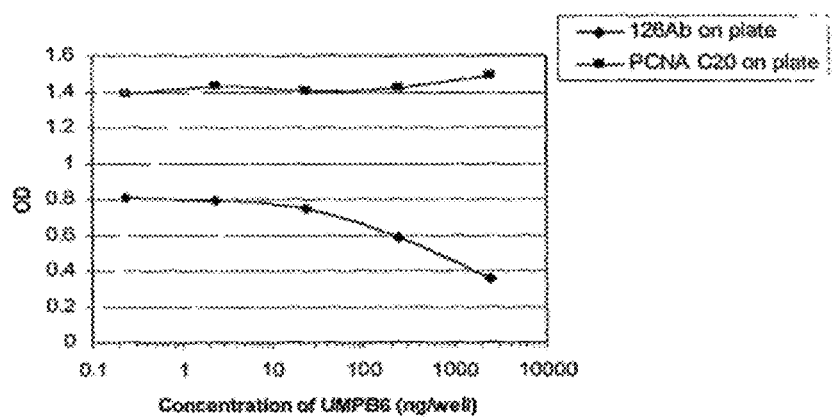
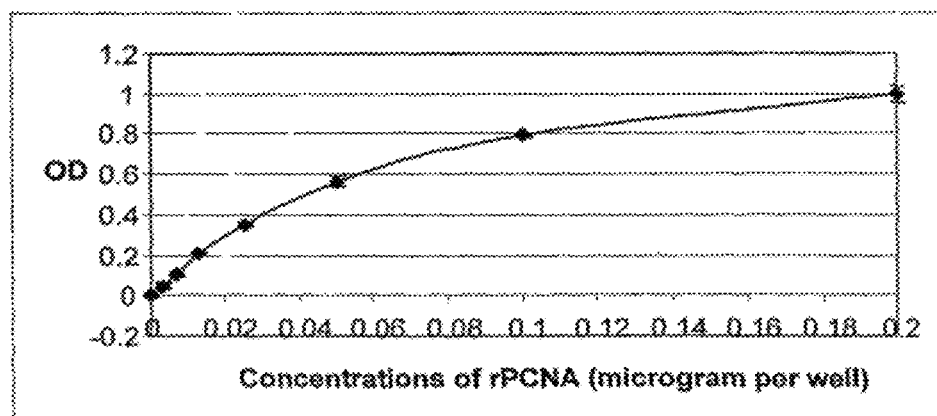
FIG. 15

SEQUENCE LISTING

<160> NUMBER OF SEQ ID NOS: 18

<210> SEQ ID NO 1
<211> LENGTH: 8
<212> TYPE: PRT
<213> ORGANISM: Homo sapiens

<400> SEQUENCE: 1

Leu Gly Ile Pro Glu Gln Glu Tyr
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Gly Gly Gly Leu Gly Ile Pro Glu Gln Glu Tyr
1               5                   10

<210> SEQ ID NO 3
<211> LENGTH: 261
<212> TYPE: PRT
<213> ORGANISM: Homo sapiens

<400> SEQUENCE: 3

Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
                20                  25                  30

Ser Gly Val Asn Leu Gln Ser Met Asp Ser Ser His Val Ser Leu Val
            35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
    210                 215                 220

Val Thr Leu Ser Met Ser Ala Asp Val Pro Leu Val Val Glu Tyr Lys
225                 230                 235                 240

```
Ile Ala Asp Met Gly His Leu Lys Tyr Tyr Leu Ala Pro Lys Ile Glu
                245                 250                 255

Asp Glu Glu Gly Ser
            260

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Asp Val Glu Gln Leu Gly Ile Pro Glu Gln Glu Tyr
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Glu Gln Leu Gly Ile Pro Glu Gln Glu Tyr
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gly Ile Pro Glu Gln Glu Tyr Ser Cys Val Val Lys
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Gly Ile Pro Glu Gln Glu Tyr Ser Cys Val Val Lys Met Pro Ser
1               5                   10                  15

Gly

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Gln Leu Gly Ile Pro Glu Gln Glu Tyr
1               5                   10
```

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Leu Gly Ile Pro Glu Gln Glu Tyr
1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gly Ile Pro Glu Gln Glu Tyr Ser Cys Val Val Lys Met Pro Ser
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Gly Ile Pro Glu Gln Glu Tyr Ser Cys Val Val Lys Met Pro
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Gly Ile Pro Glu Gln Glu Tyr Ser Cys Val Val Lys Met
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Gly Ile Pro Glu Gln Glu Tyr Ser Cys Val Val
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 14

Leu Gly Ile Pro Glu Gln Glu Tyr Ser Cys Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Gly Ile Pro Glu Gln Glu Tyr Ser Cys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gly Ile Pro Glu Gln Glu Tyr Ser
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Val Glu Gln
1

<210> SEQ ID NO 18
<211> LENGTH: 100
<212> TYPE: PRT
<213> ORGANISM: Homo sapiens

<400> SEQUENCE: 18

Leu Val Phe Glu Ala Pro Asn Gln Glu Lys Val Ser Asp Tyr Glu Met
1               5                   10                  15

Lys Leu Met Asp Leu Asp Val Glu Gln Leu Gly Ile Pro Glu Gln Glu
                20                  25                  30

Tyr Ser Cys Val Val Lys Met Pro Ser Gly Glu Phe Ala Arg Ile Cys
            35                  40                  45

Arg Asp Leu Ser His Ile Gly Asp Ala Val Val Ile Ser Cys Ala Lys
        50                  55                  60

Asp Gly Val Lys Phe Ser Ala Ser Gly Glu Leu Gly Asn Gly Asn Ile
65                  70                  75                  80

Lys Leu Ser Gln Thr Ser Asn Val Asp Lys Glu Glu Ala Val Thr
                85                  90                  95

Ile Glu Met Asn
            100
```

CSPCNA ISOFORM ANTIBODIES AND USES THEREOF

CROSS REFERENCE TO RELATED APPLICATIONS

This application is a continuation application of U.S. application Ser. No. 11/912,704, filed on Oct. 26, 2007, which is a U.S. national application under 35 U.S.C. §371 of PCT Application Serial No. PCT/US2006/016096 filed on Apr. 27, 2006, which claims the benefit under 35 U.S.C. §119(e) of U.S. Provisional Application Ser. No. 60/675,275 filed Apr. 27, 2005 and U.S. Provisional Application Ser. No. 60/689,614, filed Jun. 9, 2005, the disclosures of which are hereby incorporated herein by reference.

GOVERNMENT RIGHTS

This invention was made with government support under grant number R01CA083199 awarded by the National Institutes of Health. The Government has certain rights in the invention.

FIELD

The present disclosure relates to detection and treatment of malignant cells involving the use of antibodies that bind specifically to a cancer specific protein.

BACKGROUND

One of the least understood and most complex disease processes is the transformation that occurs as a cell becomes malignant. This process involves both genetic mutations and proteomic transformations, the result of which allows the cell to escape normal controls; preventing inappropriate cell division. All cancers are unique and distinct from other cells, as well as other cancers. Despite this uniqueness, cancer cells share some common attributes. Most cancer cells proliferate outside of the normal cell cycle controls, exhibit morphological changes and exhibit various biochemical disruptions to cellular processes.

Cancer is usually diagnosed when a tumor becomes visible well after the first on-set of cellular changes. Many cancers are diagnosed after a biopsy sample is examined by histology for morphologic abnormalities, evidence of cell proliferation and genetic irregularities. Effective treatment for malignancy often depends on the ability to detect reliably the presence of malignant cells at early stages of a disease so that an effective treatment can begin at a stage when the disease is most susceptible to such treatment. Thus, there is a need to be able to reliably detect a potentially malignant cell that has not progressed to the histological stage recognized as malignant, but which can progress to a malignant state. There is also a need for a rapid, minimally invasive technique that can reliably detect or treat malignant cells or potentially malignant cells.

Proliferating cell nuclear antigen (PCNA) is a 29 kDa nuclear protein and its expression in cells during the S and G2 phases of the cell cycle, makes the protein a good cell proliferation marker. It has also been shown to partner in many of the molecular pathways responsible for the life and death of the cell. Its periodic appearance in S phase nuclei suggested an involvement in DNA replication. PCNA was later identified as a DNA polymerase accessory factor in mammalian cells and an essential factor for SV40 DNA replication in vitro. In addition to functioning as a DNA sliding clamp protein and a DNA polymerase accessory factor in mammalian cells, PCNA interacts with a number of other proteins involved in transcription, cell cycle checkpoints, recombination, apoptosis, and other forms of DNA repair. Besides being diverse in action, PCNA's many binding partners are linked by their contributions to the precise inheritance of cellular functions by each new generation of cells. PCNA may act as a master molecule that coordinates chromosome processing.

Malignant cancer cells express an isoform of PCNA termed cancer specific PCNA (csPCNA) and non-malignant cells express an isoform termed non-malignant PCNA (nmPCNA). Effective compositions and methods to distinguish the two isoforms are needed for diagnosis and treatment of cancers.

SUMMARY

Antibodies to cancer specific isoform of proliferating cell nuclear antigen (csPCNA) and uses thereof are disclosed. Antibodies specifically bind to the cancer specific isoform of PCNA but do not bind to the non-malignant isoform of PCNA (nmPCNA). The antibodies are produced from an immunogen that includes a peptide comprising an amino acid sequence found on the region of csPCNA protein that interacts with the Xeroderma pigmentosum group G (XPG).

A peptide region that corresponds to amino acid residues 126-133 of the human PCNA protein, SEQ ID NO.: 1 (LeuGlyIleProGluGlnGluTyr) is a suitable antigenic peptide for generating csPCNA antibodies. The antigenic peptides disclosed herein may include additional amino acid residues that improve immunogenicity of the peptide without substantially interfering with the specificity of the resulting antibodies to csPCNA. For example, the peptide may have the amino acid sequence of SEQ ID NO: 2 (CysGlyGlyGlyLeuGlyIleProGluGlnGluTyr). The resulting antibodies may be polyclonal or monoclonal antibodies or fragments thereof.

An isolated antibody disclosed herein specifically binds cancer specific proliferating cell nuclear antigen (csPCNA) isoform. The csPCNA isoform includes an amino acid sequence of SEQ ID NO: 3 and any variations, mutations including substitutions, insertions and deletions that do not affect the specificity of csPCNA specific antibodies. csPCNA specific antibodies do not bind to nmPCNA isoform.

In an embodiment, the antibody binds to an epitope that includes an amino acid sequence within the csPCNA protein that binds to Xeroderma pigmentosum group G (XPG) protein.

In an embodiment, the antibody binds to an epitope of csPCNA that includes an amino acid sequence selected from LGIPEQEY (SEQ ID NO: 1), VEQLGIPEQEY (SEQ ID NO: 5), LGIPEQEYSCVVK (SEQ ID NO: 6), LGIPEQEYSCVVKMPSG (SEQ ID NO: 7), EQLGIPEQEY (SEQ ID NO: 8), QLGIPEQEY (SEQ ID NO: 9), LGIPEQEYSCVVKMPS (SEQ ID NO: 10), LGIPEQEYSCVVKMP (SEQ ID NO: 11), LGIPEQEYSCVVKM (SEQ ID NO: 12), LGIPEQEYSCVV (SEQ ID NO: 13), LGIPEQEYSCV (SEQ ID NO: 14), and LGIPEQEYSC (SEQ ID NO: 15).

In an embodiment, the antibody includes a monoclonal antibody or a chimeric antibody or a recombinant antibody or a single chain antibody.

In an embodiment, the antibody is an antibody fragment selected from Fab, Fab', or $F(ab')_2$.

The antibodies may be associated with a detectable agent and the detectable agent is selected from a fluorescent label, radio label, chromatogenic label, and an enzymatic label.

A composition includes an isolated and substantially purified antibody that is specifically bound to an epitope of cancer specific proliferating cell nuclear antigen (csPCNA), wherein the epitope includes an amino acid sequence of LeuGly-IleProGluGlnGluTyr (SEQ ID NO: 1).

A method for detecting a cancer specific proliferating cell nuclear antigen (csPCNA) isoform in a biological sample includes the steps of:

contacting the biological sample with an antibody that specifically binds cancer specific proliferating cell nuclear antigen (csPCNA) isoform;

providing conditions for the antibody binding; and detecting the binding of the antibody with the csPCNA isoform.

In an embodiment, the biological sample is a bodily fluid selected from blood, plasma, lymph, serum, pleural fluid, spinal fluid, saliva, sputum, urine, gastric juice, pancreatic juice, ascites fluid, synovial fluid, milk, and semen. Any bodily fluid is suitable so long as it is suspected of containing csPCNA isoform or PCNA isoform.

In an embodiment, the biological sample is a tissue sample selected from breast, prostrate, lung, colon, epithelial, connective, cervical, esophageal, brain, thymus, thyroid, pancreas, testis, ovary, intestine, bladder, stomach, soft tissue sarcomas, osteosarcoma, leukemia, lymphoma, carcinoma, adenocarcinoma, placenta, fibrous, germ cell tissue, and extracts thereof.

In an embodiment, the antibody detection step is performed in vivo or in vitro.

In an embodiment, the antibody detection is performed by providing a labeled secondary antibody. In another embodiment, the antibody that specifically binds cancer specific proliferating cell nuclear antigen (csPCNA) isoform is labeled. In another embodiment, the detection of csPCNA isoform bound to a csPCNA specific antibody is performed using a mass spectrometric analysis. In an embodiment, the detection of csPCNA isoform is performed using an enzyme linked immunosorbent assay. In an embodiment, the detection of csPCNA isoform is performed using an immunohistochemical method. Detection of csPCNA isoform that is either bound to a csPCNA specific antibody or isolated using a csPCNA specific antibody is not limited by any particular detection technique.

A method for diagnosing or prognosing malignancy includes the steps of: detecting csPCNA in a biological sample obtained from an animal by an antibody that specifically binds cancer specific proliferating cell nuclear antigen (csPCNA) isoform; and diagnosing malignancy based on the detection of csPCNA in the biological sample. In an embodiment, the animal is a vertebrate animal or a mammal.

A method for producing antibodies specific to a cancer specific proliferating cell nuclear antigen (csPCNA) isoform includes the steps of:

administering to an antibody generation source an immunogenic amount of a peptide representing an epitope that is exposed only on the csPCNA isoform, but not on a non-malignant isoform (nmPCNA), wherein the peptide is selected from contiguous or non-contiguous amino acid residues on the region of csPCNA that interacts with a Xeroderma pigmentosum group G (XPG) protein;

providing conditions for antibody generation; and isolating and purifying the antibodies.

In an embodiment, the antibodies are isolated and purified from hybridoma cells.

In an embodiment, the immunogenic peptide includes the amino acid sequence of CGGGLGIPEQEY (SEQ ID NO: 2). In an embodiment, the peptide is associated with a carrier protein. In an embodiment, the carrier protein is keyhole limpet hemocyanin (KLH). Any suitable carrier protein can be used with the peptides of the present disclosure.

A method to identify the location of a tumor in vivo, the method includes the steps of:

administering a cancer specific proliferating cell nuclear antigen (csPCNA) isoform specific antibody that binds csPCNA, wherein the antibody is labeled with a detectable agent; and determining the location of the tumor by detecting the accumulation of the labeled csPCNA-specific antibody at the tumor site.

A method to augment reduction of tumor progression in a subject includes the steps of:

providing a pharmaceutically acceptable composition comprising a formulation of a therapeutically effective amount of cancer specific proliferating cell nuclear antigen (csPCNA) isoform-specific antibody and a delivery component;

administering the formulation into a subject; and reducing the progression of tumor by delivering the formulation comprising csPCNA-specific antibody to the tumor site, wherein the csPCNA-specific antibody reacts with csPCNA isoform present in tumor cells.

In an embodiment, the formulation includes a liposome or a nanoparticle. In an embodiment, the formulation includes a tumor killing agent or an immune enhancing agent.

A method of identifying an anti-cancer agent includes the steps of:

contacting a population of cancer cells with an agent;

measuring the levels of a cancer specific proliferating cell nuclear antigen (csPCNA) isoform by assaying the binding of a csPCNA-specific antibody to the csPCNA isoform; and determining that the agent is an anticancer agent if the levels of csPCNA isoform in the cancer cells contacted with the agent is less than the levels of csPCNA isoform in cancer cells not contacted with the agent.

In an embodiment the agent is a small molecule or a peptide or a nucleic acid.

In an embodiment, the population of cancer cells is selected from a cancer cell line, xenograft and an orthotopic model system of cancer.

In an embodiment, determining whether the agent is an anticancer agent includes measuring the levels of non-malignant PCNA isoform in normal cells contacted with the agent and in normal cells not contacted with the agent. In an embodiment, the identification of the anti-cancer agent is performed in a high-throughput system.

An immunoassay kit for detecting the csPCNA isoform of PCNA includes the following components:

an antibody preparation that specifically binds only to a cancer specific proliferating cell nuclear antigen (csPCNA) isoform and not to the normal proliferating cell nuclear antigen (nmPCNA) isoform, whereby the antibodies and csPCNA form a complex;

and reagents for detecting the complex.

Positive control peptides in the kit may include peptide of amino acid sequences selected from LGIPEQEY (SEQ ID NO: 1), VEQLGIPEQEY (SEQ ID NO: 5), LGIPEQEYSCVVK (SEQ ID NO: 6), LGIPEQEYSCVVKMPSG (SEQ ID NO: 7), EQLGIPEQEY (SEQ ID NO: 8), QLGIPEQEY (SEQ ID NO: 9), LGIPEQEYSCVVKMPS (SEQ ID NO: 10), LGIPEQEYSCVVKMP (SEQ ID NO: 11), LGIPEQEYSCVVKM (SEQ ID NO: 12), LGIPEQEYSCVV (SEQ ID NO: 13), LGIPEQEYSCV (SEQ ID NO: 14), and LGIPEQEYSC (SEQ ID NO: 15).

In an embodiment, the csPCNA isoform is used as a positive control in the immunoassay kit.

An isolated auto-antibody specific to a cancer specific proliferating cell nuclear antigen (csPCNA) isoform is disclosed. In an embodiment, the auto-antibody is complexed to an epitope of csPCNA isoform.

A method of determining the presence of malignant cells includes the steps of:

contacting a biological sample suspected of containing auto-antibodies, to a substrate comprising bound cancer specific proliferating cell nuclear antigen (csPCNA) isoform or fragments thereof, wherein the auto-antibodies are specific to a csPCNA isoform;

providing conditions for csPCNA-auto-antibody complex formation; and detecting the presence of the auto-antibody-csPCNA complex in the biological sample.

In an embodiment, the presence of the auto-antibody-csPCNA complex is detected using an anti-human secondary antibody. In an embodiment, the presence of the auto-antibody-csPCNA complex is detected using a labeled biological sample.

A method of detecting the presence of a circulating cancer specific proliferating cell nuclear antigen (csPCNA) isoform, the method includes the steps of detecting an auto-antibody specific to the csPCNA isoform in a biological sample and thereby determining the presence of circulating csPCNA isoform.

A method of monitoring the remission status of an individual includes the steps of:

detecting the presence of proliferating cell nuclear antigen (csPCNA) isoform in the individual prior to and after cancer therapy; and determining the remission status of the individual by comparing the levels of circulating csPCNA isoform prior to and after cancer therapy.

In an embodiment, the csPCNA isoform is detected by determining the presence of auto-antibodies to csPCNA isoform. In an embodiment, the csPCNA isoform is detected by an antibody specific to the csPCNA isoform.

Additional features of the present disclosure will become apparent to those skilled in the art upon consideration of the following detailed description of embodiments exemplifying the best mode of carrying out the subject matter of the disclosure as presently perceived.

BRIEF DESCRIPTION OF THE DRAWINGS

FIG. 1 shows a sequence listing including SEQ ID NOS.: 1-4.

FIG. 2 shows results of Western blots using PC 10, Ab121 and Ab126 antibodies.

FIG. 14 shows auto-antibody levels in patients with cancer.

FIGS. 15 (A-C) shows the specificity and sensitivity of a csPCNA antibody ("Ab126").

DETAILED DESCRIPTION

Figure 3:
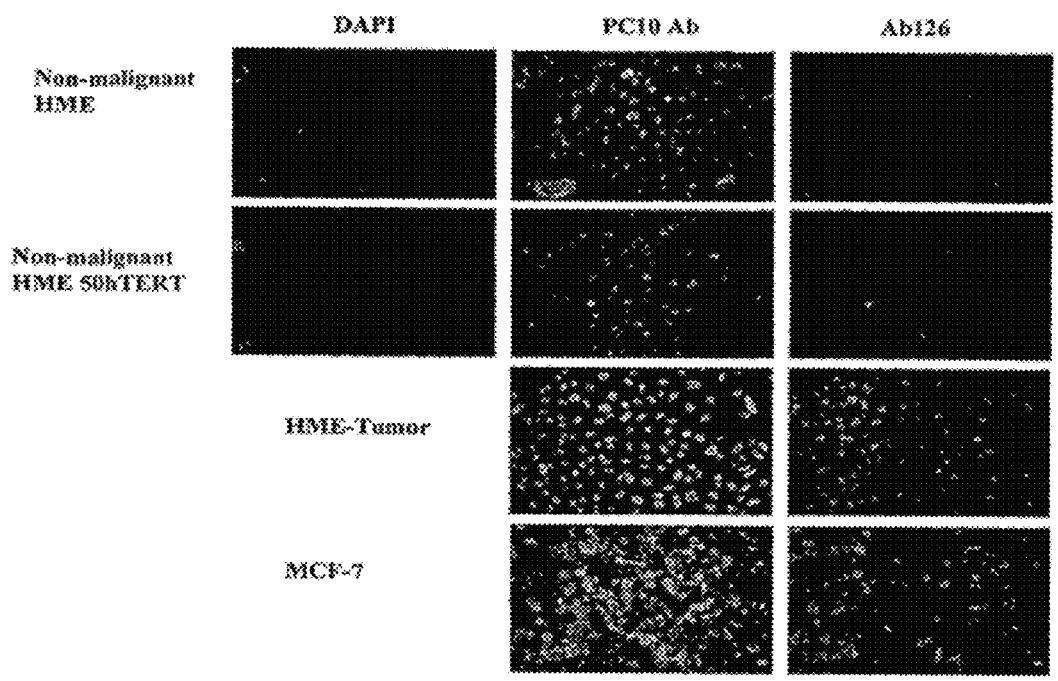
FIGS. 3-4 show results of immunofluorescent staining of cells growing in culture using PC 10 and Ab126 antibodies.

Proliferating cell nuclear antigen (PCNA) protein is altered in cancer cells. PCNA is a 28 kD protein with an electrophoretic mobility equivalent to that of a 36 kDa protein. PCNA is an accessory factor required by DNA polymerase 5 to mediate highly efficient DNA replication activity. The DNA synthesome purified from a malignant cell contains at least two forms of PCNA. The two forms have the same molecular weight, as measured on a Western blot of a two-dimensional polyacrylamide gel stained with a commercially available antibody which specifically binds to PCNA (PC 10, Oncogene Science, Cambridge Mass.). However, the two species of PCNA differ significantly in their overall charge. Thus, an acidic, malignant or cancer specific, form of PCNA, csPCNA, and a basic, nonmalignant or normal, form of PCNA, nmPCNA, can be distinguished on a two-dimensional polyacrylamide gel.

The acidic csPCNA is expressed in malignant cell lines, such as HeLa (human cervical carcinoma), Hs578T (breast carcinoma), HL-60 (human promyelogenous leukemia), FM3A (mouse mammary carcinoma), PC 10 (prostate carcinoma), LNCaP (prostate carcinoma), LN99 (prostate carcinoma) MD-MB468 (human breast carcinoma), MCF-7 (breast carcinoma), KGE 90 (esophageal-colon carcinoma), KYE 350 (esophageal-colon carcinoma), SW 48 (esophageal-colon carcinoma) and T98 (malignant glioma). The acidic csPCNA is also expressed in malignant cells obtained from human breast tumors, prostate tumors, brain tumors, human gastrointestinal or esophageal-colon tumors, murine breast tumors and in human chronic myelogenous leukemia. The acidic csPCNA is not detected in nonmalignant cell lines, such as the breast cell lines Hs578Bst and MCF-10A, or in samples of nonmalignant serum or tissue, such as breast.

Commercially available antibodies do not distinguish between csPCNA and nmPCNA. Thus, commercially available anti-PCNA antibodies cannot be used to specifically detect only the malignant form of PCNA.

An isolated and purified preparation of antibodies is provided that can specifically detect csPCNA isoform. The antibody preparations disclosed herein are substantially pure. For example, csPCNA-specific antibody preparation is about 90% pure or about 95% pure. The preparation includes antibodies that specifically bind only to the csPCNA isoform and not to the nmPCNA isoform. The affinity constant for csPCNA antibody and csPCNA antigen binding can range from a factor of about $10^8$/mol to above $10^{11}$/mol.

The preparation of antibodies contains the antibodies that bind to an epitope present on csPCNA, but not on nmPCNA. In an aspect, the epitope is formed from contiguous or non contiguous amino acid residues within the csPCNA protein region that binds to Xeroderma pigmentosum group G (XPG) protein. The term "epitope" herein refers to a localized region on the surface of an antigen which antibody molecules can identify and bind.

In another aspect, the preparation of antibodies contains antibodies that bind to an epitope comprising an amino acid sequence of SEQ ID NO.: 1.

In another embodiment, a method for producing antibodies specific to csPCNA is provided. The method comprises the step of administering to a test animal, an immunogenic amount of a peptide representing an epitope present only on the csPCNA, but not on nmPCNA. The peptide comprises an amino acid sequence that includes from 5 to 50 amino acid residues within the region of csPCNA that binds to the XPG protein. The peptide may include 5 to 12 contiguous or from 13 to 20 or 30 non-contiguous amino acid residues, and may also include the amino acid residues in the interdomain connector loop region (amino acid residues 121 to 135). The peptide may be administered as many times as necessary to ensure the effective production of polyclonal antibodies in the test animals. The polyclonal antibodies are subsequently purified.

In an additional embodiment, a method for producing monoclonal antibodies is provided. The method comprises the steps of administering to a test animal, which is usually a mouse, an immunogenic amount of a peptide representing an epitope present only on the csPCNA, but not on nmPCNA. The peptide contains an amino acid sequence selected from 5 to 12 contiguous or from 13 to 50 non-contiguous amino acid residues of the region of csPCNA that binds to the XPG protein. The peptide may be administered as many times as necessary to ensure the effective production of antibodies in the mouse. The spleen cells of the test animal is subsequently harvested and prepared for the production of hybridoma cells. The hybridoma cells are subjected to selection for those producing csPCNA monoclonal antibodies. The selected hybridoma cells are grown in an appropriate medium, and the monoclonal antibodies are purified from the hybridoma medium.

In a specific embodiment, the peptide used as the immunogen to generate antibodies comprises the amino acid sequence of SEQ ID NO.: 1 (LeuGlyIleProGluGlnGluTyr).

Peptides having amino acid sequence of SEQ ID NO.: 1 (LeuGlyIleProGluGlnGluTyr) and one or more additional amino acid residues are suitable for generating antibodies as long as the specificity to csPCNA is maintained. The additional amino acids can include amino acids derived from PCNA or from another source or randomly chosen. The additional amino acids can also include amino acids to improve stability and immunogenicity. For example, in a more specific embodiment, the peptide used as the immunogen to generate antibodies comprises the amino acid sequence of SEQ ID NO.: 2 (CysGlyGlyGlyLeuGlyIleProGluGlnGluTyr). Further, the antibodies can be purified by any method well known in the art. For example, monoclonal or polyclonal antibodies are affinity purified, by passing antiserum or medium over a chromatography column or modified filter membrane to which the antibodies will bind. The bound antibodies can then be eluted from the column, for example using a buffer with a high salt concentration or an altered pH.

In another embodiment, peptides capable of generating csPCNA specific antibodies include peptides of amino acid sequences that include about +3 contiguous or non contiguous additional amino acids on the NH2 terminus of SEQ ID NO: 1 (LGIPEQEY) and about +9 contiguous or non contiguous amino acids on the COOH terminus of LGIPEQEY. For example, some of these peptides include amino acid sequences of VEQLGIPEQEY (+3—NH$_2$ terminus, SEQ ID NO: 5), LGIPEQEYSCVVK (+5—COOH terminus, SEQ ID NO: 6), LGIPEQEYSCVVKMPSG (+9—COOH terminus, SEQ ID NO: 7), EQLGIPEQEY (+2—NH$_2$ terminus, SEQ ID NO: 8), QLGIPEQEY (+1—NH$_2$ terminus, SEQ ID NO: 9), LGIPEQEYSCVVKMPS (+8—COOH terminus, SEQ ID NO: 10), LGIPEQEYSCVVKMP (+7—COOH terminus, SEQ ID NO: 11), LGIPEQEYSCVVKM (+6—COOH terminus, SEQ ID NO: 12), LGIPEQEYSCVV (+4—COOH terminus, SEQ ID NO: 13), LGIPEQEYSCV (+3—COOH terminus, SEQ ID NO: 14), LGIPEQEYSC (+2—COOH terminus, SEQ ID NO: 15), LGIPEQEYS (+1—COOH terminus, SEQ ID NO: 16) and combinations of the additional NH$_2$ and COOH termini amino acids that flank LGIPEQEY (SEQ ID NO: 1). Amino acid mutations including substitutions that do not affect the specificity of the peptides to generate csPCNA specific antibodies are within the scope of this disclosure. One or more of the amino acid residues in the peptides may be replaced with an amino acid analog or an unnatural amino acid. In addition, peptide mimetics developed based on the sequences of the peptides disclosed herein, can also be used to generate antibodies to csPCNA isoform.

In another embodiment, a method for detecting a cancer specific proliferating cell nuclear antigen (csPCNA) isoform is provided. The method comprises the step of contacting a biological sample comprising a csPCNA isoform with the preparation of antibodies, whereby the antibodies and the csPCNA isoform form a complex; and the step of detecting the complex.

A biological sample can be a body fluid sample, which may include blood, plasma, lymph, serum, pleural fluid, spinal fluid, saliva, sputum, urine, semen, tears, synovial fluid or any bodily fluid that can be tested for the presence of csPCNA isoform. Alternatively, the biological sample can be a tissue sample, wherein the cells of the tissue sample may be suspected of being malignant. For example, tissue sections or cell cultures can be mounted on glass or plastic slides and contacted with the antibodies according to standard immunocytochemical protocols. Tissue extracts or concentrates of cells or cell extracts are also suitable. The antibodies can include a detectable label, such as a colorimetric, radioactive, fluorescent, chemiluminescent, enzymatic, or a biotinylated moiety. Specific binding between the antibodies and the csPCNA can be detected using secondary antibodies. Many systems for the detection of bound antibodies are known in the art. Alternatively, an enzyme linked immunosorbent assay (ELISA), radioimmunoassay (RIA), colorimetric, fluorometric, and surface plasmon resonance (SPR) can be used to detect specific binding of the antibodies in solubilized cells, cell extracts, liquid samples, and bound to solid substrate. The antibodies of the present disclosure can also be used in Western blots of one- or two-dimensional polyacrylamide gels which have been used to separate proteins from the cells or tissues to be tested. Such methods are familiar and widely practiced in the art. Antibodies specific to csPCNA isoform are used to capture the circulating csPCNA isoform or fragments thereof and the identity of csPCNA isoform or fragments thereof can be confirmed using mass spectrometric methods.

In another embodiment, a method for diagnosing malignancy is provided. The method comprises the step of immuno-detecting csPCNA in a biological sample obtained from a person or particularly a patient suspected of having a malignant condition, wherein the immuno-detecting csPCNA step involves the use of the preparation of antibodies disclosed herein.

In another embodiment, a method to aid in diagnosing malignancy is provided. The method comprises the step of immuno-detecting csPCNA in a tissue sample, wherein cells of the tissue sample are suspected of being malignant, and wherein the immuno-detecting csPCNA step involves the use of the preparation of antibodies disclosed herein. It is to be understood that the malignant cells that can be detected using the antibodies, but are not limited to, malignant cells in tissues such as breast, prostate, blood, brain, pancreas, smooth or striated muscle, liver, spleen, thymus, lung, ovary, skin, heart, connective tissue, kidney, bladder, intestine, stomach, adrenal gland, lymph node, or cervix, or in cell lines, for example, Hs578T, MCF-7, MDA-MB468, HeLa, HL60, FM3A, BT-474, MDA-MB-453, T98, LNCaP, LN 99, PC 10, SK-OV-3, MKN-7, KGE 90, KYE 350, or SW 48.

In another embodiment, a method to aid prognosis of the development of malignancy is provided. The method involves immuno-detecting csPCNA in a tissue sample using the antibodies disclosed herein, wherein cells of the tissue sample may be suspected of being malignant, and correlating the levels of csPCNA with the progression of a particular malignant disease. Furthermore, the antibodies can be used to prognose the potential survival outcome for a patient who has developed a malignancy. It is to be understood that the diseases which can be diagnosed or prognosed using the antibodies include, but are not limited to, malignancies such as various forms of glioblastoma, glioma, astrocytoma, meningioma, neuroblastoma, retinoblastoma, melanoma, colon carcinoma, lung carcinoma, adenocarcinoma, cervical carcinoma, ovarian carcinoma, bladder carcinoma, lymphoblastoma, leukemia, osteosarcoma, breast carcinoma, hepatoma, nephroma, adrenal carcinoma, or prostate carcinoma, esophageal carcinoma. If a malignant cell expresses csPCNA isoform, the antibodies disclosed herein are capable of detecting the csPCNA isoform.

Antibodies disclosed herein also detect malignancy in some of the tumor types in breast tissue that include ductal cysts, apocrine metaplasia, sclerosing adenosis, duct epithelial hyperplasia, non-atypical, intraductal papillomatosis, columnar cell changes, radial sclerosing lesion (radial scar), nipple adenoma, intraductal papilloma, fibroadenoma, lactating papilloma, atypical duct epithelial hyperplasia, atypical lobular hyperplasia, ductal carcinoma in situ—sub classified as nuclear grades 1, 2, and 3, lobular carcinoma-in-situ, pleomorphic lobular carcinoma-in-situ, infra-mammary lipoma, mammary hamartoma, granular cell tumor, intramammary fat necrosis, pseudoangiomatous stromal hyperplasia (PASH), malignant melanoma involving the breast, malignant lymphoma involving the breast, phyllodes tumor—benign, borderline, and malignant subclasses, and sarcoma of the breast.

In another embodiment, the antibodies disclosed herein are used to determine the malignancy stage in tumors, by comparing levels of csPCNA in a tumor over time, to follow the progression of a malignant disease, or a patient's response to treatment.

The antibodies can also be used to detect malignant cells which have broken free from a tumor and are present in a patient's bloodstream, by using the antibodies to assay a blood sample for the presence of the csPCNA isoform. The biological sample can be obtained from human patients or veterinary patients. It is to be understood that the concentration of antibody to be used will depend on the particular antibody and its affinity for the csPCNA. Typically, antibody affinities are from about $10^4$ $M^{-1}$ to about $10^9$ $M^{-1}$. Concentrations of antibodies used in the immunochemical methods discussed above can be, for example, approximately 50 to about 2000 nanograms of antibody per ml, or up to 50-500 μg per ml.

In another embodiment, an immunoassay kit for detecting the csPCNA isoform is provided. The kit comprises the antibodies that bind only to csPCNA, and can include additional components, for example, reagents such as blocking antiserum, secondary antibodies, buffers, or labeling reagents for carrying out immunochemical staining, ELISAs, or RIAs with the antibodies. The kit can also include positive controls (e.g., csPCNA isoform or peptides thereof or a malignant tissue or cell sample) and negative controls (e.g., non-malignant tissue sample). The kit can also include instructions for using the kit as a diagnostic or prognostic aid for malignancies.

In another embodiment, an assay system for screening test compounds for the ability to suppress a malignant phenotype of a cell is provided. The kit includes the antibodies disclosed herein that bind only to csPCNA and a sample of viable malignant cells.

In another embodiment, the csPCNA-specific antibodies can be used in assays to screen test compounds for the ability to suppress a malignant phenotype of a cell or potential anti-tumor or anti-cancer compounds. The assay comprises contacting a malignant cell with a test compound and observing the levels of csPCNA using the antibodies disclosed herein. The test compound can be a pharmacologic compound already known in the art to have an effect on a malignant phenotype or other pharmacological effect, or can be a compound previously unknown to have any pharmacological activity. The test compound can be naturally occurring or designed in the laboratory. The test compound can be isolated from a microorganism, animal, or plant, or can be produced recombinantly or synthesized by chemical methods known in the art. A test compound also includes nucleic acids, peptides, peptide nucleic acids (PNAS), anti-sense oligos, siRNA nucleic acids, and other antibodies. A test compound which decreases the expression of the csPCNA isoform decreases levels of DNA synthetic activity of a purified synthesome, or increases levels of replication fidelity of a purified DNA synthesome is a potential therapeutic agent for suppressing a malignant phenotype and for treating malignancy.

In yet another embodiment, the antibodies can also be used as therapeutic agents, to restore the normal function of PCNA in a malignant cell. The antibodies can be delivered to a malignant cell in a human or veterinary patient using any method known in the art. For example, full-length antibodies, antibody fragments, or antibody fusion proteins which bind specifically to csPCNA in malignant cells, can be administered to such patients. A therapeutic cocktail that includes csPCNA-specific antibodies can be delivered inside a tumor. The therapeutic composition is administered soon after obtaining a positive result using a diagnostic method disclosed herein. Both the dose and the means of administration of the therapeutic compositions can be determined based on the specific qualities of the composition, the condition, age, and weight of the patient, the progression of the particular disease being treated, and other relevant factors. Administration can be local or systemic, including injection, oral administration, catheterized administration, and topical administration.

It is to be understood that a receptor-mediated targeted delivery of therapeutic compositions containing the antibodies is used to deliver the antibodies to specific tissues. Many tumors, including breast, lung, and ovarian carcinomas, over-express antigens specific to malignant cells, such as glycoprotein $p185^{HER2}$. Antibodies which specifically bind to these antigens can be bound to liposomes which contain an antibody specific to csPCNA. When injected into the bloodstream of a patient, the anti-$p185^{HER2}$ antibody directs the liposomes to the target cancer cells, where the liposomes are endocytosed and thus deliver their contents to the malignant cell (Kirpotin et al., *Biochem.* 36: 66, 1997).

Liposomes can be loaded with the antibody as is known in the art (see Papahadjopoulos et al., *Proc. Natl. Acad. Sci.* 88: 11640, 1991; Gabizon, *Cancer Res.* 52: 891, 1992; Lasic and Martin, *Stealth Liposomes,* 1995; Lasic and Papahadjopoulos, *Science* 267: 1275, 1995; and Park et al., *Proc. Natl. Acad. Sci.* 92: 1327, 1995). Such liposomes contain about 0.02-0.15 mg of csPCNA specific antibody per μmol liposome and can be administered to patients in a range of about 5 mg/kg. The therapeutic composition can include a pharmacological excipient, such as but not limited to etoposide or cytosine arabinoside, or adriamycin.

Auto-antibodies against specific cellular proteins associated with a tumor cell occur during the growth of many types of tumors. These antibodies are used to identify the presence of malignancy based on the fact that the antigenic proteins giving rise to the auto-antibodies are not generally found freely circulating in healthy individuals. Thus, the presence of these freely circulating proteins is indicative of disease and could be useful either directly as a marker for disease, or the detection of auto-antibody to one or more of these proteins could serve as an indicator for the presence of disease. The presence of auto-antibody to csPCNA in the serum of stage IV breast cancer patients sampled prior to treatment with chemotherapy demonstrates the presence of free circulating csPCNA.

In another aspect, auto-antibodies specific to csPCNA were identified and isolated. The term auto-antibody herein refers to antibody that is made by the immune system of the body. The recognition that csPCNA can be found circulating in the blood-stream of advanced or late stage cancer patients, and the immunohistochemical data showing that the antibody to csPCNA can be used to identify the presence of cancer cells at a single cell level, indicated that the expression of individuals with cancer also produce auto-antibodies to csPCNA. Because this cancer specific protein is not generally encountered by the cells of the immune system in the body of healthy individuals, csPCNA is not recognized as "self". These auto-antibodies to csPCNA therefore also serve as a predictor of the presence of malignancy. In addition, the presence of these auto-antibodies demonstrates that it is possible to mount a strong immune response to the cancer cells producing csPCNA, and that they might be useful as tools for identifying the site(s) within the body at which the cancer cells reside. Furthermore, antibody production generally represents several fold increase in number compared to the antigen and therefore, auto-antibodies to csPCNA increase the sensitivity of detection in a detection assay.

The auto-antibody specific to the csPCNA can be isolated from a biological sample such as a malignant tissue or serum, using any suitable method known in the art. The auto-antibody can also be isolated in the form of an auto-antibody-csPCNA complex. The bound csPCNA isoform can be separated from the complex and identified using csPCNA specific antibodies described herein. In an embodiment, the auto-antibody specific to the csPCNA isoform may be identified using a human anti-IgG or other suitable detection reagent. For example, csPCNA may be used to bind to the auto-antibody specific to the csPCNA isoform then the bound csPCNA isoform in turn is immuno-detected using the csPCNA specific antibody described herein. Alternatively, the csPCNA protein may be labeled with a detectable agent, for example, a fluorescence dye, prior to the binding assay.

In another embodiment, the presence of the auto-antibody specific to the csPCNA isoform detected in a fluid or a tissue may be used as an indicator of malignancy. The detection of the auto-antibody specific to csPCNA may also indicate the tissue site of malignant cells. In addition, the presence of this specific auto-antibody may be used as a prognostic indicator for assessing the likelihood of long-term survival, or as a monitoring tool to determine the remission status of a patient following a surgery to remove tumor or a cancer therapy. The antibody turnover and loss of csPCNA expression, upon removal of the primary tumor, would be expected to significantly reduce the levels of circulating auto-antibody to csPCNA. Further, this specific auto-antibody provides a basis for implying that a vaccine targeting csPCNA, and the cells at the sites secreting the protein into the blood stream, can be targeted for destruction by generation of a cytotoxic immune response.

The term "antibody" includes monoclonal antibodies (including full length monoclonal antibodies), polyclonal antibodies, multispecific antibodies (e.g. bispecific antibodies), and antibody fragments so long as they exhibit the desired biological activity or specificity.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or epitope. Furthermore, each monoclonal antibody is directed against a single determination site on the antigen. Monoclonal antibodies may be made by a variety of methods, including but not limited to the hybridoma method first described by Kohler et al., Nature 256:495 (1975), or may be made by recombinant DNA methods (e.g., U.S. Pat. No. 4,816,567). The monoclonal antibodies may also be isolated from phage antibody display libraries using the technique described in Clackson et al., Nature 352:624-626 (1991) and Marks et al., J. Mol. Biol. 222:581-597 (1991). Producing monoclonal antibody generally requires immunizing an animal, e.g., a mouse; obtaining immune cells from its spleen; and fusing the cells with a cancer cell (such as cells from a myeloma) to make them immortal. A tumor of the fused cells is called a hybridoma, and these cells secrete mAb. The development of the immortal hybridoma generally requires the use of animals. A hybridoma cell line that secretes mAb that reacts strongly with csPCNA isoform or fragments thereof is selected. The cells grow and multiply to form a clone that will produce the desired mAb. There are generally two methods for growing these cells—injecting them into the peritoneal cavity of a mouse or using in vitro cell-culture techniques. When injected into a mouse or any suitable animal, the hybridoma cells multiply and produce fluid (ascites) in its abdomen. This ascites fluid contains a high concentration of antibody. Another alternative is to grow hybridoma cells in a tissue-culture medium in a small scale batch system or a large scale batch reactor.

In vitro production of mAb usually requires growth of hybridoma cultures in batches and purification of the mAb from the culture medium. Serum-free tissue culture media formulated to support the growth of hybridoma cell lines is available. Cell cultures are allowed to incubate in commonly used tissue-culture flasks under standard growth conditions for about 10 days. mAb is then harvested from the medium. Growth of hybridoma cells to higher densities in culture results in larger amounts of mAb that can be harvested from the media. The use of a barrier such as a hollow fiber or a membrane, with a low-molecular-weight cutoff (10,000-30,000 kD) is suitable to grow the hybridoma cells at high densities. These semi-permeable-membrane-based systems isolate the cells and the mAbs are produced in a small chamber separated by a barrier from a larger compartment that contains the culture media. Culture can be supplemented with growth factors that help optimize growth of the hybridoma. For a general review of antibody production and purification protocols, see *Current Protocols in Molecular Biology*, Ed. Ausubel et al., John Wiley & Sons Inc, (1988).

The monoclonal antibodies herein include "chimeric" antibodies (immunoglobulins) in which the portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

Phage display methodology can also be used to produce csPCNA specific antibodies. This technique uses bacteria and bacterial viruses known as phage to produce and select synthetic antibodies that have all the target-recognition specificity of antibodies produced by the immune system. These synthetic antibodies are produced using the same genes that code for the target-recognition or variable region in natural antibodies from mammalian systems. The phages are genetically engineered so that a particular antibody is fused to a protein on the phage's coat and the gene encoding the displayed antibody is contained inside the phage particle. This technology thus couples the displayed antibody's phenotype to its genotype, allowing the DNA that codes for the selected antibody to be retrieved easily for future use. Collections of these antibody-covered phages are called a library.

To select the phage with the desired antibody from a library, the phages are allowed to bind to the target molecule, which is attached to a solid surface. The phage with antibodies that recognize the target molecule bind tightly, and the remaining (unbinding) phage are simply washed away. Phage display permits to select antibodies with different binding characteristics for a given target. The DNA contained within the desired phage then can be used to produce more of the selected antibody for use in research or medical diagnostics.

Phage peptide display methodology can be used to identify peptides that bind csPCNA specific antibodies. For example, a library of a variety of peptides that range from about 6 amino acids to about 12 or 15 amino acids including variants of a peptide or protein is expressed on the outside of a phage virion, while the genetic material encoding each of those peptides resides inside the phage particle. This creates a physical linkage between each variant protein sequence and the DNA encoding it facilitating rapid identification based on binding affinity to a given target molecule, such as csPCNA specific antibodies by a selection process called panning. For example, panning is carried out by incubating a library of phage-displayed peptides with a plate or bead or any solid substrate coated with csPCNA specific antibody, washing away the unbound phage, and eluting the specifically bound phage. The eluted phage is then amplified and followed by additional binding/amplification cycles to enrich the pool for binding sequences. After 3-4 rounds, individual clones are characterized by DNA sequencing and ELISA. csPCNA antibodies can also be used to identify synthetic peptide libraries for peptides or peptide inimetics that bind csPCNA specific antibodies.

Ribosome display is a cell-free display technology, which uses in vitro cellular components that are involved in protein synthesis, to create libraries containing billions of different human antibody fragments and from which in turn, antibodies to target molecules can be rapidly isolated.

Ribosome display technology can also be used to identify antibodies to target molecule such as csPCNA. This methodology is based on the formation of stable antibody-ribosome-mRNA complexes and has similarities with phage display in that the antibody protein is directly linked to its encoding DNA sequence. Libraries of antibody genes extracted from human cells are copied and amplified by standard PCR. After transcription, a population of mRNA molecules, each coding for a different antibody gene. The mRNA molecules are then incubated with lysate-based ribosomes (bacteria derived ribosomes and their protein making machinery), which translate the mRNA into protein complexes, a ribosome display library. Such complexes, each displaying a different antibody, are mixed with the target antigenic peptide such as, for example, peptides derived from csPCNA isoform and those antibodies that are specific to the target bind to it and non-binders are washed away.

Complexation or conjugation of primary antibodies, e.g., csPCNA antibodies or secondary antibodies with dye—or enzyme—labeled Fab fragments of secondary antibodies directed against their Fc regions are within the scope of this disclosure. A plurality of labels are available for coupling or conjugating to a primary or a secondary antibody including but not limited to Aminomethylcoumarin (AMCA), Fluorescein (FITC), Fluorescein (DTAF), Rhodamine (TRITC), Texas Red™, Cy2™, Cy3™, cy5™, cy7™, R-Phycoerythrin (RPE), B-Phycoerythrin (BPE), C-Phycocyanin, R-Phycocyanin. For Horseradish peroxidase (HRP)—3-amino-9-ethylcarbazole (AEC, red) and Diamino benzidine (DAB, brown); for alkaline phosphatase (AP)—Fast red (pink), bromochloroindolyl phosphate (BCIP, yellow), iodonitrotetrazolium violet (INT) (reddish brown), Nitroblue tetrazolium (NBT, purple), New Fuchsin (red), TNBT (purple), and Vega red (pink). Any detectable label that can be associated with an antibody is suitable for using with csPCNA-specific antibodies.

EXAMPLES

The following examples are provided for the purpose of exemplification only and are not intended to limit the disclosure which has been described in broad terms above.

Example 1

Production of csPCNA Specific Antibodies

This example is to demonstrate the production of peptide specific antibodies that bind only to csPCNA, and not nmPCNA.

Human csPCNA and nmPCNA isoforms have identical amino acid sequences that are identified herein as SEQ ID NO: 3. As shown in the sequences in FIG. 1, the csPCNA or the nmPCNA contains 261 amino acid residues.

An immunogen of PCNA disclosed herein may be a peptide having an amino acid sequence selected from the region spanning between amino acid residues 75 and 150 of SEQ ID NO.: 3. PCNA amino acid sequence may include mutations such as insertions, deletions, substitutions that do not affect the specificity of the binding of csPCNA antibodies. Peptides or fragments of PCNA or csPCNA relate to short contiguous or non contiguous sequences in PCNA. The peptide may contain an amino acid sequence that includes at least the sequence from Leu126 to Tyr133 of the PCNA or SEQ ID NO.: 1 (LeuGlyIleProGluGlnGluTyr). Additional amino acids may also be added for the purpose of increasing immunogenicity or antigenicity without substantially affecting the specificity. For example, conservative amino acid substitutions can be made without altering the specificity. Based on the guidance provided herein, synthetic peptides can also be made to generate antibodies that are specific to csPCNA isoform. Any suitable procedure for producing peptides may be employed to produce the immunogens disclosed herein.

Example 1A

Peptide Specific Antibodies

Two synthetic peptides were made that had sequences identified as SEQ ID NO.: 2 (CysGlyGlyGlyLeuGlyIleProGluGlnGluTyr) and the second peptide had a sequence identified as SEQ. ID NO.: 5 (CysAspValGluGlnLeuGlyIleProGluGlnGluTyr). SEQ ID NO.: 5 includes a portion of the immunodominant region of PCNA (AspValGluGln). The two synthetic peptides were used to generate polyclonal antibodies in rabbits, using the procedure known in the art. The resulting antibodies were identified as Ab126 (generated from SEQ ID NO.: 1) and Ab121 (generated from SEQ ID NO.: 5).

Western blot analysis was performed to evaluate the antibodies' ability to specifically recognize csPCNA. Protein samples prepared from the high speed supernatant (S3) of MCF-7 breast cancer cell line and PA-1 ovarian cancer cell line were resolved by 2D-PAGE. Western blot analysis of the resolved polypeptides was then performed using Ab126, Ab121, or PC 10 (a commercially available anti-PCNA antibody). As shown in FIG. 2, PC 10 antibody, like other commercially available antibodies to PCNA, recognizes both the basic isoform, nmPCNA, found in non-malignant cells, and the acidic isoform, csPCNA, found exclusively in cancer cells. It is noted that both cancer cell lines, MCF-7 (FIG. 2A) and PA-1 (FIG. 2B), used in the present experiments produce detectable nmPCNA. The non-specific binding property of the commercially available antibodies renders them unable to distinguish between malignant and non-malignant cells. The comparative analysis of the antibodies demonstrates the ability of the Ab 126 antibody to specifically recognize csPCNA in Western blots of both breast cancer cell and ovarian cancer proteins. However, the Western blot using Ab121 does not show the specificity towards the csPCNA. Like PC 10 antibody, Ab121 recognizes both the csPCNA and the nmPCNA isoforms. Thus, it was unexpected that the peptide that contains a portion of the immunodominant region of PCNA yielded non-specific antibodies, while the peptide that does not contain any portion of the immunodominant region of PCNA yielded csPCNA specific antibodies.

Monoclonal antibodies using the above-described peptide are prepared. Traditional methods of monoclonal antibody production may be employed as well as the approach using the HuCal GOLD® recombinant antibody library and phage display technique to identify human anti-csPCNA antibody. The resulting monoclonal antibodies would also specifically recognize only the csPCNA isoform.

Example 1B

AB126 Antibody Specifically Recognizes Cancer Cells Grown in Culture

Two different types of cell staining analyses were performed to evaluate whether Ab126 antibody (hereinafter may be referred to as csPCNAab) could distinguish between malignant and non-malignant breast cells. The results demonstrate that the Ab 126 antibody has high specificity for cancer cells and that it serves as an early detector for malignancy. An immunofluorescence cell staining experiment was performed using the Ab126 antibody (FIG. 3). Non-malignant human mammary epithelial cells (HME) and non-malignant HME cells immortalized with the telomerase gene (HME50hTERT) were used. Neither the HME nor HME50hTERT cells have the ability to raise tumors in nude mice. In addition, malignant HME cells derived from a patient with breast cancer (HME-Tumor) as well as malignant MCF-7 cells were used. These different cell types were stained with green fluorescent-labeled anti-PCNA (PC 10) antibody and red-labeled Ab126. Neither PC 10, nor any other antibody commercially available for PCNA, or Ab121 can be used to distinguish non-malignant from malignant human cells because all of these antibodies are prepared to an immunodominant region within the PCNA molecule, whereas Ab 126 or csPCNAab is made to a region of PCNA that is distal to the immunodominant region. As can be seen in FIG. 3 the labeled PC 10 antibody readily stains all the different cell types examined, both malignant and non-malignant. However, the labeled Ab126, made specifically against csPCNA, does not stain non-malignant cells but is able to readily detect cancer cells. DAPI staining of the non-malignant cells, which stains the nucleus of these cells, does show the presence of cells in the field and staining with PC-10 shows that PCNA is present in these normal cells and that it is not the cancer specific isoform of PCNA. This example demonstrates that Ab126 detects cancer cells specifically and, thereby, supports the premise that csPCNA is a biomarker for malignancy.

Example 1C

AB126 Antibody Recognizes Early Stage Cancer Cells

Figure 4:
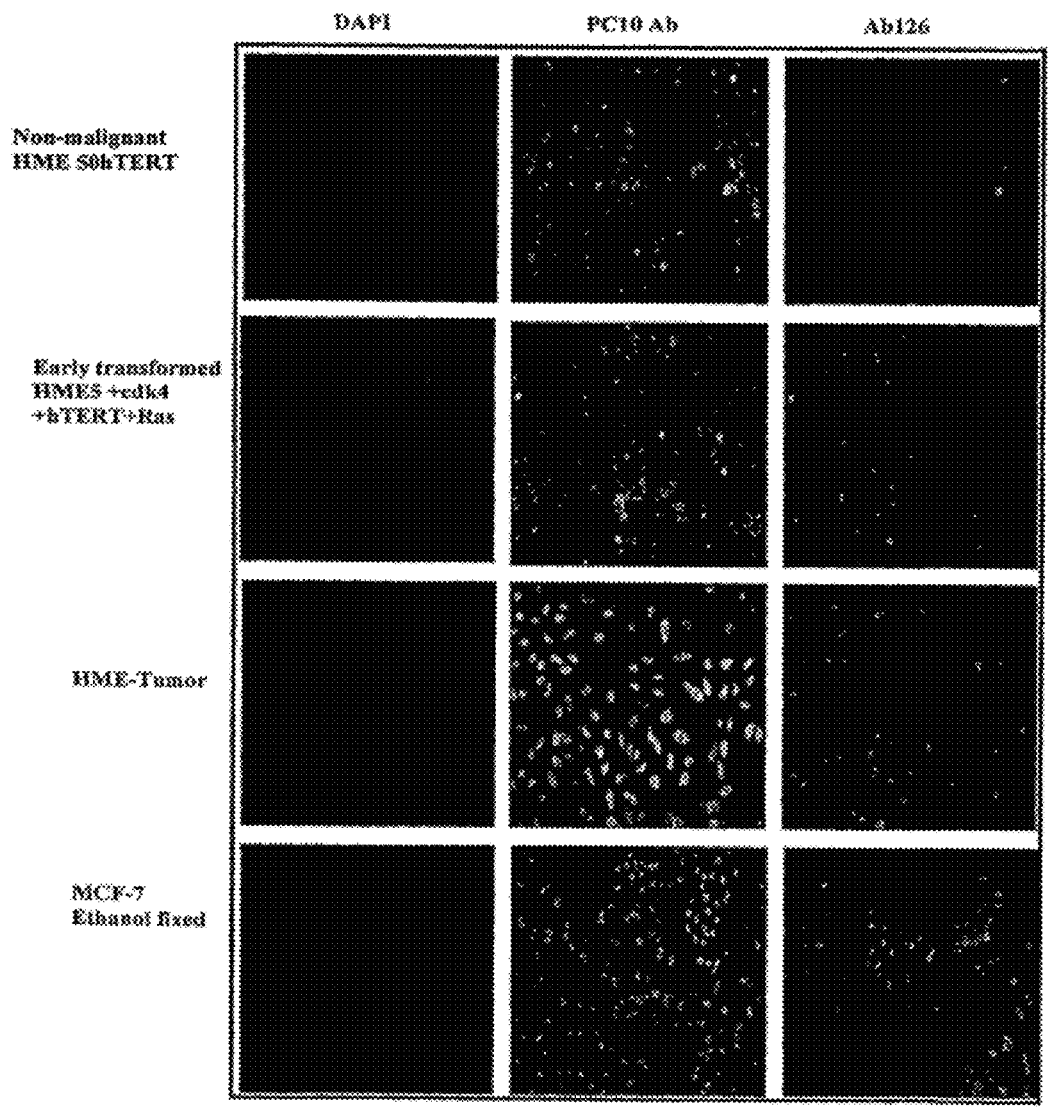

This example demonstrates that Ab126 antibody recognizes early stage cancer cells for faster diagnosis. Non-malignant HME50hTERT cells as well as malignant HME-Tumor and MCF-7 cells were used in immunofluorescence staining experiments. In addition, HME cells transfected with telomerase, cdk4 and Ras were evaluated as well (HME5+cdk4, hTERT+Ras). When introduced into mice, these cells produce tumors, but only after a prolonged time. It is believed that they may represent very early transformed cells. In the experiment, as shown in FIG. 4, all of the cell types were stained with DAPI to demonstrate the presence of cells in each magnification field. Labeled PC10 antibody stained all the different cell types. However, the cancer specific Ab126 antibody does not label non-malignant cells, but does readily label malignant cells. In addition, the Ab126 antibody labeled the HME5+cdk4+hTERT+Ras cells, indicating the presence of csPCNA in early transformed cells.

Example 1D

AB126 Antibody Specifically Recognizes Cancer Cells in Tissue

Figure 5:
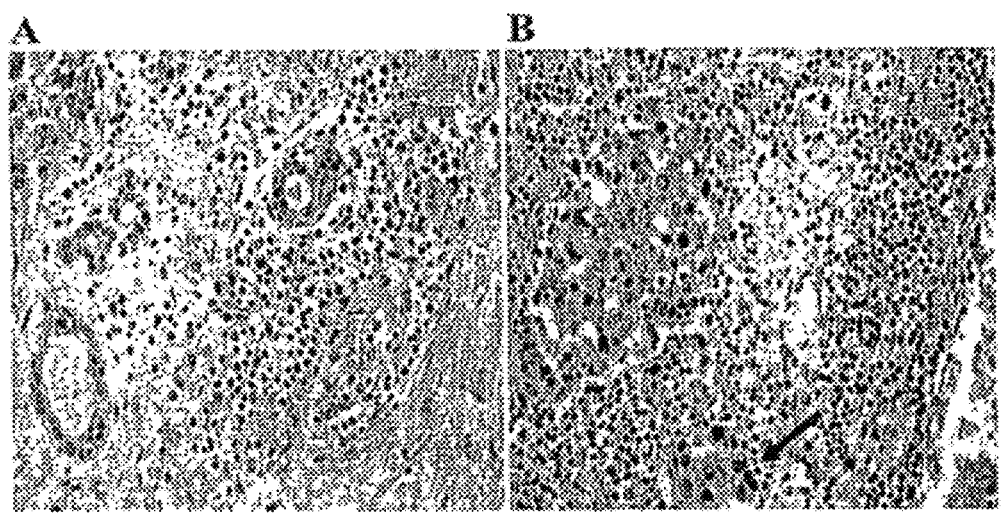
FIG. 5 shows results of immunohistochemical staining of cells in paraffin embedded tissue sections using Ab126 antibodies.

Immunohistochemical staining of malignant and non-malignant paraffin embedded breast tissue specimens was also performed with the Ab126 antibody. The results are shown in FIG. 5 (panels A&B). The results show the ability of the antibody to specifically recognize only the cancer cells that are present only in panel B. The cells in both panels are also counter stained with Hematoxylin and Eosin (H&E) stain to identify the nuclei. Cells staining with Ab126 antibody appear brown (panel B).

The examples demonstrate that the Ab 126 or other antibodies produced in accordance with the methods disclosed herein can be used to specifically identify the csPCNA isoform, and that the csPCNA isoform is a bona fide marker of malignancy. Accordingly, the Ab126 antibody or the like is useful for monitoring the remission status of individuals being treated for cancer. Ab126 or the like is a useful reagent for developing ELISA and immunohistochemical assays for screening purposes. In addition, Ab126 or the like is useful for identifying individuals with early stage cancers, by identifying malignancy potential in either the body fluid or in the cell or tissues of the individual. The antibody may also be useful for identifying its location of a tumor by radiolabeling or fluorescent labeling the antibody and allowing it to react with the csPCNA being released in the vicinity of a tumor by tumor cells. Ab126 or the like is a useful member of a panel of antibodies that have the ability to recognize markers currently used to evaluate tumors for their malignancy potential.

Example 2 csPCNA-Specific Antibody Recognizes Malignant Breast Cancer Cells

Figure 6:
FIG. 6 shows that csPCNAab antibody specifically recognizes csPCNA. Sixty μg of MCF7 cell extract were subjected to 2D-PAGE and Western blot analysis. The PC10 and csPCNAab antibodies were used at a dilution of 1:1000 in the Western blot analysis.

This example demonstrates that an anti-csPCNA antibody selectively recognizes breast cancer cells from normal cells. Using an amino acid sequence derived from PCNA, a commercial antibody vendor ((Zymed, Inc., San Francisco, Calif.) was contracted to produce csPCNA-specific antibodies. A rabbit polyclonal antibody that selectively identified the csPCNA isoform and not the nmPCNA isoform, was produced. This specificity of csPCNA-specific antibody was confirmed by Western blots, immuno-fluorescent staining of both human breast cell lines and human tumor/normal tissue, and by DAB based immuno histochemical staining (IHC). Animal immunization utilized a peptide fragment of PCNA coupled to Keyhole Limpet Hemacyanin through four cysteines added to the amino terminal portion of the peptide. 100 micrograms of the KLH conjugated peptide fragment selected from the region spanning amino acids 100-160 of PCNA, was resuspended in complete Freund's adjuvant, and injected subcutaneously into multiple sites in 2 female New Zealand White rabbits. The rabbits were rested for one month prior to boosting the animals with a second 100 μg dose of the KLH coupled antigen in incomplete adjuvant. Antibody titer to the antigen was determined by ELISA assay approximately 10-14 days post-immunization, and after an additional 14 day rest period, the animals received a second boost of KLH coupled antigen. 12 days later, 25 ml of antisera was collected from each rabbit and stored at −20° C. The antisera was dialyzed against two changes of 20 mM phosphate buffered saline, pH 7.0, and loaded onto a protein G Sepharose column pre-equilibrated with the same buffered saline. The binding capacity of the gel was 19 mg of rabbit IgG/ml of packed gel bed. The column was washed with 10 column volumes of PBS, and eluted with 10 volumes of 0.1 M glycine buffer, pH 3.0. One milliliter fractions eluting from the column were collected at a flow rate of 1-2 ml per minute into 0.25 ml of 0.25M Tris-HCl pH 8.0. The concentration of protein in fractions containing the protein peak eluting from the column was determined by Bradford assay, and these fractions were combined and dialyzed against phosphate buffered saline containing 10 mM NaN3 prior to being stored at 4° C., until used in various assays. Western blot analysis of the resolved polypeptides was then performed using either commercially available anti-PCNA PC10 antibody or rabbit polyclonal antibody (FIG. 6). PC10 antibody, like the commercially available antibodies to PCNA, recognizes both the basic isoform of PCNA (nmPCNA) found in non-malignant cells, and the acidic isoform of PCNA (csPCNA) found exclusively in breast cancer cells. csPCNA antibody specifically recognizes the csPCNA isoform in 2D-PAGE Western blot analysis of cancer cell extracts.

Example 2A

Figure 7:
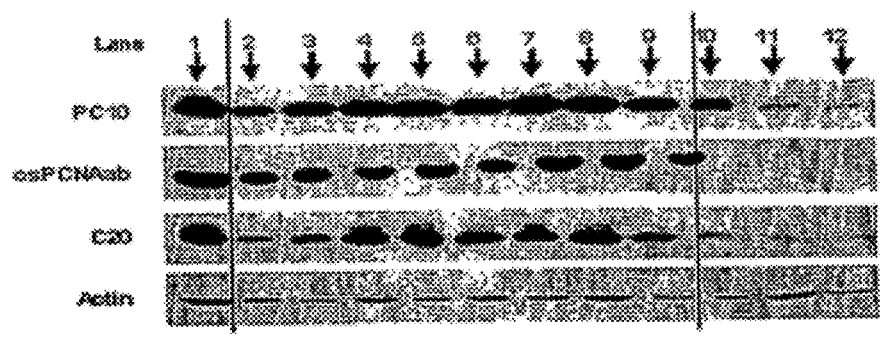
FIG. 7 shows that csPCNAab antibody specifically recognizes the form of PCNA uniquely expressed in malignant cells. Lane 1, MCF cell extract (serves as a marker for PCNA). Lanes 2-9, breast cancer tissue extracts. Lanes 10-12, normal breast tissue extracts. The films were exposed overnight.
Figure 8:
FIG. 8 shows that high concentrations of csPCNAab in Western blot analysis do not recognize the PCNA isoform present in non-malignant breast tissues. 200 μg of tissue extracts, prepared from either a woman with breast cancer or a disease free woman, were subjected to 2D-PAGE and Western blot analysis using published procedures. The PC10 and csPCNAab antibodies were used at dilutions of 1:250, 1:500, or 1:1000 in the Western blot analysis. Lane 1, MCF cell extract (serves as a marker for PCNA). Lanes 2, 4, 6, breast cancer tissue extract probed using PC10 antibody used at a dilution of 1:1000, 1:500 or 1:250, respectively. Lanes 3, 5, 7, non-malignant breast tissue extract probed using PC10 antibody used at a dilution of 1:1000, 1:500 or 1:250, respectively. Lanes 8, 10, 12, breast cancer tissue extract probed using csPCNAab used at a dilution of 1:1000, 1:500 or 1:250, respectively. Lanes 9, 11, 13, non-malignant breast tissue extract probed using csPCNAab used at a dilution of 1:1000, 1:500 or 1:250, respectively.

Comparative Selectivity Analysis of Breast Cancer Tissue Specimens Using csPCNAab A panel of normal breast tissue and breast cancer tissue specimens was analyzed by Western blotting for the presence of PCNA using either commercially available antibodies or csPCNAab (FIG. 7). The commercial antibodies included: C20, an antibody to the C-terminus of PCNA, and PC 10, which was prepared against the entire rat PCNA protein. The commercial antibodies recognized the PCNA present in either the normal or malignant breast tissues. However, the csPCNAab antibody only detected the presence of PCNA in malignant tissues. This ability of csPCNAab was due to csPCNA being expressed in the malignant cells and not in normal cells. The specificity of the antibody for the csPCNA isoform was further demonstrated in an experiment in which increasing concentrations of either the commercially available PC 10 antibody or csPCNAab were used in Western blot analysis of non-malignant and malignant tissue extracts for PCNA detection (FIG. 8). The results of this experiment demonstrate that even at high concentrations of the csPCNAab in the Western analysis, the antibody only detected the presence of csPCNA in cancer tissue. Whereas, at all concentrations the PC10 antibody readily detected PCNA protein in both malignant and non-malignant breast tissue.

Example 2C csPCNAab Specifically Detects Breast Cancer Cells in Culture and Tissue

Figure 9:
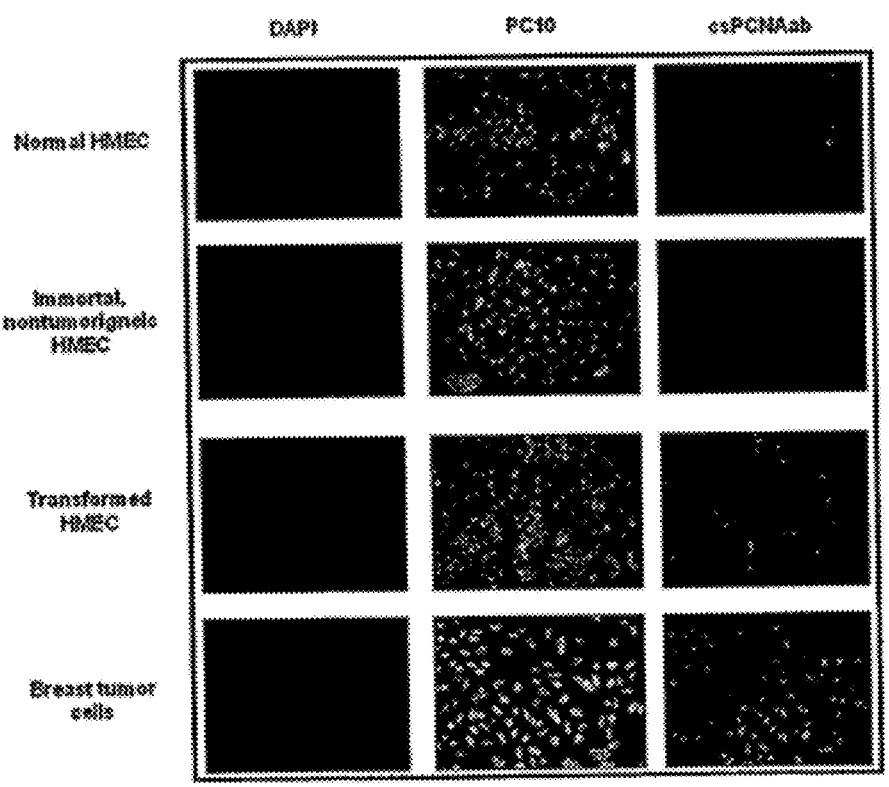
FIG. 9 shows that tumorigenic breast epithelial cells express csPCNA while non-tumorigenic breast epithelial cells do not. The human mammary epithelial cells (HMECs) used for these experiments were grown under serum-free conditions. To obtain the non-tumorigenic yet immortalized cell line, HMECs were derived from a 31-year-old Li-Fraumeni Syndrome (LFS) patient's non-cancerous breast tissue (containing a germ line mutation at codon 133 in one of the two alleles of the p53 gene (Met to Thr [M133T]) that affects wild-type p53 protein conformation). These cells undergo crisis around population doubling (PD) level 50-60 and spontaneously immortalize with a frequency of 5 in 10 million. A transformed HME cell line was established by infecting the pre-immortal HME cells with hTERT and H-RasV12 then collecting clones that grew in soft agar and nude mice xenografts (Herbert et al., manuscript in preparation). MCF-7 breast carcinoma cells were grown in DMEM (Invitrogen, Carlsbad, Calif.) containing 10% cosmic calf serum (HyClone, Logan, Utah) and 50 μg/ml gentamicin (Invitrogen, Carlsbad, Calif.). Cells were subjected to immunofluorescence staining with either mouse anti-PC10 (recognizing all forms of PCNA) or rabbit csPCNAab (recognizing csPCNA). Cells grown on cover slips overnight were fixed with 4% paraformaldehyde and permeabilized with 0.1% Triton X-100 before blocking with 3% BSA. Staining was performed with the PCNA antibodies diluted in PBS with 0.5% sodium azide and an Alexa-Fluor 468 anti-mouse IgG or Alexa-Fluor 568 anti-rabbit IgG conjugated secondary antibody (Molecular Probes, Eugene, Oreg.). The coverslips were mounted with Vectashield containing DAPI (Vector Laboratories, Burlingame, Calif.) and cells were examined using a Leica fluorescent microscope. Cells were counterstained with DAPI and viewed with a Leica fluorescent microscope using a 20× objective.
Figure 10:
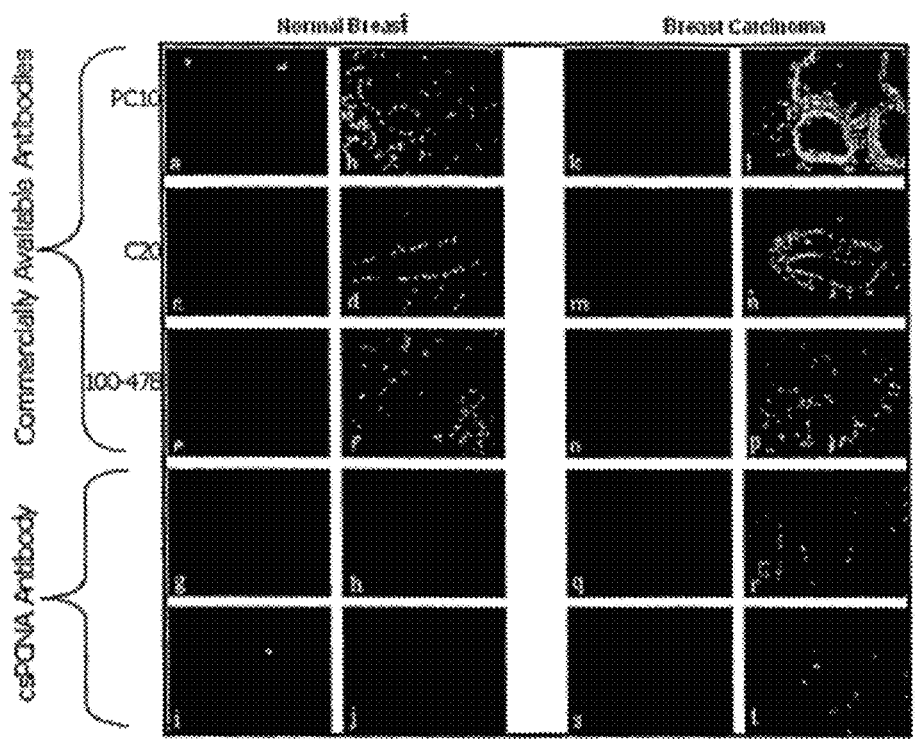
FIG. 10 shows that csPCNAab antibody specifically recognizes breast carcinoma cells. Normal breast tissue sections were from 3 different patients: (a-b, e-f), (c-d, g-h), (i-j, k-l); Breast carcinoma tissue sections were from 3 different patients: (m-n, q-r), (o-p, s-t), (u-v, w-x). Paraffin-embedded tissues cut in 3 μm sections and placed on glass slides, were incubated in xylene twice for 10 min each to remove the paraffin. Slides were rehydrated with a series of ethanol washes (100-90-80-70-0% in dH20) for 10 min each. Antigen retrieval was performed using the Antigen Unmasking Solution (Vector Laboratories, Burlingame, Calif.). Slides were placed in blocking buffer (3% BSA in PBS) for 30-60 min at room temperature. Either mouse PC10, C20, 100-478 antibodies or rabbit csPCNAab at 1:200 dilution in blocking buffer were placed directly onto the tissue, covered with parafilm, and incubated in humid chamber for 60 min at room temperature. After three 5-minute washes in PBS, slides were incubated with the appropriate fluorescent secondary antibody at 1:600 dilution in blocking buffer, covered with parafilm, and placed in a humidified chamber for 30-60 min at room temperature in the dark. Another series of three 5-minute washes were performed in PBS and the slides were mounted with Vectashield™ containing DAFT. Tissue sections were examined using a Leica fluorescent microscope with a 20× objective. DAPI served as a counterstain.

Immunofluorescence analyses were performed to evaluate whether csPCNAab could distinguish between malignant and non-malignant breast cells in cell culture and tissue specimens. The results demonstrate that the antibody has high specificity for cancer cells (FIGS. 9-10). The csPCNAab was examined for its ability to stain non-malignant and malignant breast cells grown in culture (FIG. 9). In this experiment, all of the different cell types were stained with DAPI, to demonstrate the presence of cells in each magnification field. The cells examined were normal human mammary epithelial cells (HMEC) and spontaneously immortalized HMECs that are not tumorigenic. Transformed HMECs that carried a mutation in p53 and had been transfected with the human telomerase catalytic component (hTERT) and the Ras oncogenes (H-Ras-V12) were also evaluated. In addition, transformed HMECs that were cultivated from tumors grown in athymic mice as well as MCF-7 cells were used as breast tumor cells for FIG. 9. As can be seen in FIG. 9, the commercially available PC10 antibody readily stained all of the different cell types examined, (i.e., both malignant and non-malignant). PC10 antibody has been used extensively for quantifying PCNA expression. Unlike the commercial antibodies, csPC-NAab, which selectively recognizes csPCNA, does not stain non-malignant cells but is able to readily detect breast cancer cells. DAPI staining of the non-malignant cells, shows the presence of cells in the field. A few bright red fluorescent "spots" seen in the non-malignant cultures stained with csPC-NAab are due to non-specific binding to debris, since these "spots" are seen in the same location in the cultures stained with the green-labeled PC10 antibody. This experiment shows that csPCNAab specifically detects cultured breast cancer cells.

In another experiment, fresh frozen non-malignant and malignant breast tissue specimens were also evaluated by comparative immunofluorescence staining using commercially available antibodies and the csPCNAab antibody (FIG. 10). In this study, the commercially available PC10, C20 and 100-478 (Novus) antibodies were evaluated. As illustrated in FIG. 10, all of the commercially available antibodies readily stain both non-malignant and malignant breast tissue. In contrast to the PC10, C20 and 478 antibodies, the csPCNAab only stained malignant breast tissue. These experiments, using both cells grown in culture as well as human tissue, demonstrate that csPCNAab specifically detects only breast cancer cells and offers support that csPCNA is a true marker for breast malignancy.

Example 3

Figure 12:
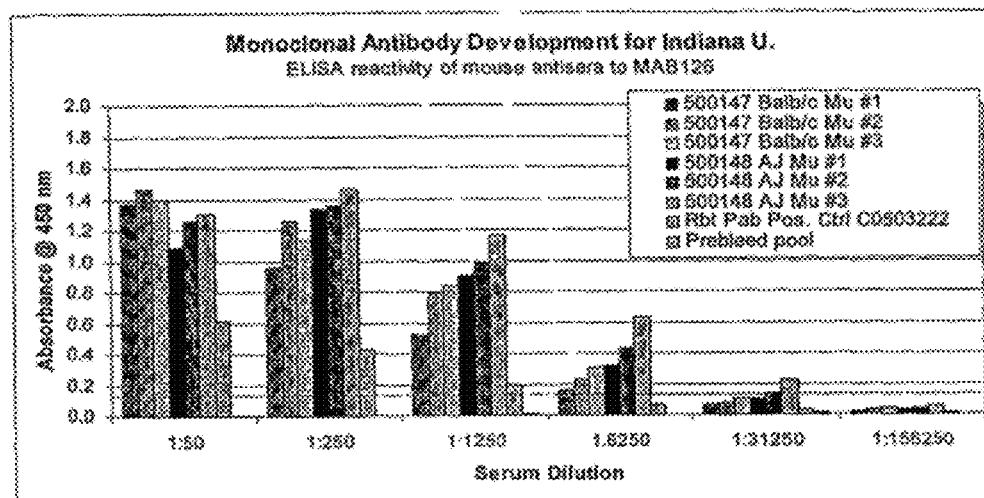
FIG. 12 shows generation of peptide specific murine polyclonal antibody to the csPCNA antigenic peptide. The peptide fragment of PCNA used to prepare the rabbit polyclonal antibody was coupled to Keyhole impet hemocyanin (KLH). 100 μg of conjugated peptide was used to immunize the mice intra peritoneally, and serum was collected by tail bleed 12 days after immunization. Sera were diluted in PBS, as indicated and incubated with antigenic peptide captured on the ELISA plate. After washing the plates with PBS, the captured murine antibody was incubated with anti-mouse IgG and color developed. Polyclonal antibody titer to csPCNA was quantified prior to selecting the mouse producing the highest level of antibody to csPCNA. The mouse spleen was removed, and spleen cells were fused to NS-0 cells and subject to selection in HAT media.

Generation of Murine Polyclonal and Monoclonal Antibodies to csPCNA Antigenic Peptide Two strains of mice (3 mice/strain) were immunized with 100 µg of KLH conjugated csPCNA peptide fragment. csPCNA-derived peptide fragment that included amino acid positions 126-133 of the human PCNA protein, SEQ ID NO.: 1 (LeuGlyIleProGluGlnGluTyr) was used. The mice were rested and a test bleed was performed 12 days after immunization to determine whether the mice developed an immune response to the peptide. Antibody production to csPCNA peptide was determined by ELISA assay using the antigenic peptide coupled to the ELISA plate. A dilution of the mouse anti-sera was incubated with the immobilized peptide, and captured anti-csPCNA antibody was quantified following incubation with an anti-murine IgG antibody conjugated to horse radish peroxidase (HRP). All of the mice were rested for 30 days, and after the antibody titer dropped to near baseline, they were boosted with a second dose of csPCNA peptide. This process was repeated three times, and following quantification of the immunological response to csPCNA peptide, the spleen from the mouse that had the greatest immune response, was removed, (FIG. 12), and the spleen cells were fused to NS-0 myeloma cells. The murine antisera did not bind to a random peptide sequence and a peptide from a different immuno-dominant region of csPCNA were used as controls during the screen, and produced a baseline absorbance value that is not shown on the histogram (FIG. 12). Hybridomas were selected in HAT media. The hybridomas surviving HAT selection were screened for antibody production to csPCNA peptide, and 29 clones making anti-csPCNA antibody were selected. These clones were continued in HAT media for an additional 2 weeks, and 15 clones were reselected by ELISA and identified as stable antibody producing cell lines. These cell lines were subcloned by limiting dilution, and the clones producing antibody to csPCNA were selected, grown to high density and affinity purified anti-csPCNA antibody was prepared for use in Western blot following 2D-PAGE resolution of the PCNA isoforms and IHC analyses; confirming specificity for csPCNA. Five of these affinity purified monoclonal antibodies are used for detection of malignant cells in biological samples.

Example 4

Immunohistochemical (IHC) Staining of Paraffin Embedded Breast Tissue Specimens

Figure 11:
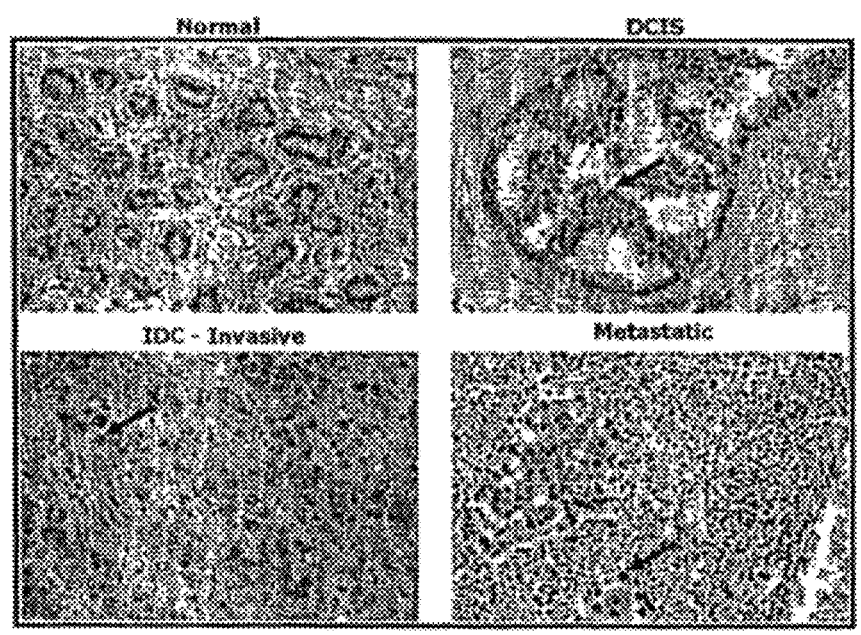
FIG. 11 shows that csPCNAab IHC detects breast cancer cells in tissue. Results are representative of normal breast tissue derived after breast reduction surgery; breast tissue from patients with DCIS; invasive breast cancer; or metastatic disease. Arrows indicate csPCNAab staining of malignant cells. 20 cases of breast cancer were selected. Also, 10 cases that showed normal breast tissue or benign fibrocystic changes were selected. IHC staining of malignant and non-malignant paraffin embedded breast tissue specimens was performed with csPCNAab with DAB as the chromogen (brown); sections were counter stained with hematoxylin stain (blue) to identify the nuclei.

This example demonstrates that csPCNA-specific antibodies and methods disclosed herein, detected malignant cells in embedded tissue specimens. Immunohistochemical staining of paraffin embedded breast tissue specimens was also performed with csPCNAab. The tissues examined were nonmalignant tissue obtained following breast reduction surgery as well as tissues from patients with ductal carcinoma in situ (DCIS), a precancerous condition characterized by the clonal proliferation of malignant-like cells in the lining of a breast duct without evidence of spread outside the duct to other tissues in the breast or outside the breast. DCIS is a precursor of invasive or metastatic disease. Representative results are illustrated (FIG. 11). These results demonstrate that csPC-NAab specifically recognizes an epitope within the nuclei of cancer cells and detects early stage (DCIS) disease. csPCNA Expression was not observed in normal breast lobules.

In as aspect, positive control slides contain duplicate sections of known invasive breast tumor cores, and a blank paraffin section serves as a negative control. In brief, 5 µm paraffin sections of the tissue specimens are fixed to positively charged slides and de-paraffinized in xylene (3 changes) and then hydrated with graded alcohols and distilled water. Antigen retrieval is performed in citrate buffer (pH 6.0) using a microwave oven for 10 min and subsequent cooling for 20 min. This is followed by blocking of endogenous peroxidase activity with Peroxo-block® (Zymed). After rinsing the slides in phosphate buffered saline (PBS), the slides are incubated with biotinylated csPCNAab (dilution: 1:400) or commercially available biotinylated PC10 antibody (Bio-Science, dilution 1:250) for 1 hr. The antigen-antibody reaction are visualized by binding avidin conjugated peroxidase (Zymed Picture Plus™ Kit: HRP/Fab polymer conjugate, Invitrogen, Carlsbad, Calif.) to the biotinylated primary antibodies and reacting the antibody-peroxidase complex with diaminobenzidine (DAB Plus®, Dako, Carpinteria, Calif.). The slides are counterstained with hematoxylin (Vector Labs), cleared in alcohol and xylene, and mounted with Histomount™ (Zymed, Invitrogen, Carlsbad, Calif.) before visualization. Substitution of primary csPCNAab or PC10 antibody by phosphate buffered saline (PBS) or isotype specific control antibody are also used as negative controls. Combined H&E stain is used to define cellular architecture and identify the nuclei of cells in each tissue section, and represents a standard method for determining the presence of malignancy in histopathological assessment. H&E is applied to tissue sections following IHC staining of the paraffin embedded specimens with either csPCNAab or PC10 antibodies.

IHC evaluation and scoring are performed as described herein. After completing the staining and initial scoring of pathology specimens and tissue arrays for reactivity with PC10 and csPCNAab antibodies, the stained slides are independently evaluated for confirmation of the staining results. Each histological section is screened and assessed for the percentage of normal and neoplastic nuclei displaying immunostaining. Immunoreactivity for csPCNAab is classified as negative, low, moderate or high if <2%, 2-20%, 21-70%, or 71-100%, of the cell nuclei, respectively, are positively stained. These chosen immunoreactivity range values are consistent with those used for clinical pathology judgment with other biomarkers for breast cancer. Any suitable scoring method can be used in addition to the ones described herein. Ten non-overlapping high power microscope fields are counted per specimen, and a specimen is classified as a breast carcinoma when at least 2% of the nuclei stain with the csPCNAab. The analysis can be re-evaluated if a consensus needs to be achieved. Proliferating malignant cells are expected to stain brown with both csPCNAab and PC10 antibodies using DAB as substrate. Normal tissue specimens are not expected to react with the csPCNAab and remain blue/purple due to the H&E stain, but proliferating cells within the normal tissue should stain brown only when probed with PC10 antibody, regardless of their proliferation rate (FIGS. 9-10).

Example 4A

Clinical Diagnosis of Malignant Breast Cancer Cells

Immunofluorescent cell and tissue staining were used o demonstrate the ability of csPCNAab to selectively bind to breast cancer cells either grown in culture, (FIG. 9), or present in malignant tissues (FIG. 10). Clinical diagnosis of malignant breast cancer is also performed by immunohistochemical staining of cancerous tissue using csPCNA-specific antibodies.

Tissue array slides from the commercial array sources and individual slides prepared from tissue specimens are analyzed for their ability to bind csPCNAab and/or PC10 antibody. Paraffin-embedded tissues cut into 3-5 µm sections are incubated in xylene twice for 10 min each to remove the paraffin. The slides are rehydrated with a series of ethanol washes (100-90-80-70-0% in $dH_2O$) for 10 min. each. Antigen retrieval is performed using the Antigen Unmasking Solution (Vector Laboratories, Burlingame, Calif.) according to instructions. Slides are then placed in blocking buffer (3% BSA in PBS) for 30-60 min at room temperature. Either mouse anti-PCNA (PC10) antibody (recognizing all isoforms of PCNA) or rabbit csPCNAab at 1:200 dilution in blocking buffer is placed directly onto the tissue, covered with parafilm, and incubated in a humid chamber for 60 min at room temperature. After three 5 min washes in PBS, slides are incubated with the appropriate fluorescent secondary antibody (Alexa 468 (green fluorescence) (Calbiochem, San Diego, Calif.) anti-mouse IgG or Alexa 568 (red fluorescence) anti-rabbit IgG; (Molecular Probes, Invitrogen, Carlsbad, Calif.)) at a 1:600 dilution in blocking buffer, covered with parafilm, and placed in a humidified chamber for 30-60 min at room temperature in the dark. Another series of three 5 min washes are performed in PBS and the slides are mounted with Vectashielde (Vector Laboratories, Burlingame, Calif.) containing DAPI. Tissue sections are examined using a Leica fluorescent microscope with a 20×, (and a 40×), objective. DAPI serves as a counterstain. Following the incubation of proliferating normal and malignant breast cells with the csPCNA and PC10 antibodies, binding of the Alexa 468 and Alexa 568 antibodies to these cells are evaluated. The Leica fluorescent microscope is equipped with red-green filters to enable to distinguish whether one or both antibodies are bound to the same breast cells. Each histological section is screened and assessed for the percentage of normal and neoplastic nuclei displaying red or green immunofluorescence. Immuno-reactivity for csPCNAab is classified as negative, low, moderate or high if <2%, 2-20%, 21-70%, or 71-100%, of the cell nuclei, respectively, fluoresce red). IHC scoring and evaluation are performed as described herein. Normal tissue specimens only fluoresce green because of their ability to only react with the PC10 antibody, while malignant cells express both isoforms of PCNA and are anticipated to react with both PC10 and csPCNAab. In addition, both slowly and rapidly proliferating cells within the normal tissue specimens are expected to bind only the PC10 antibody (FIGS. 9-10). Detecting csPCNA isoforms using csPCNA specific antibody analysis is not limited by a particular label associated with the antibody. For example, immunofluorescent staining is more sensitive than DAB staining, and because digital images of the immunofluorescently labeled serial tissue sections can be overlaid with one another, co-localization of red and green staining cells are readily confirmed for each tissue specimen analyzed, and is expected to selectively indicate the presence of malignant cells only in the cancer specimens being analyzed. The presence of red fluorescence only in the breast tumor specimens confirms the selectivity of csPCNAab for malignant breast cells.

Proliferating non-malignant breast cells, grown in culture or present in normal tissue, do not express csPCNA, and therefore do not react with csPCNAab. In contrast, they do react with the non-selective PC10 antibody.

Antibody compositions and methods disclosed herein also detect a variety of breast tumor types including ductal cysts, apocrine metaplasia, sclerosing adenosis, duct epithelial hyperplasia, non-atypical, intraductal papillomatosis, columnar cell changes, radial sclerosing lesion (radial scar), nipple adenoma, intraductal papilloma, fibroadenoma, lactating papilloma, atypical duct epithelial hyperplasia, atypical lobular hyperplasia, ductal carcinoma in situ-sub classified as nuclear grades 1, 2, and 3, lobular carcinoma-in-situ, pleomorphic lobular carcinoma-in-situ, intra-mammary lipoma, mammary hamartoma, granular cell tumor, intramammary fat necrosis, pseudoangiomatous stromal hyperplasia (PASH), malignant melanoma involving the breast, malignant lymphoma involving the breast, phyllodes tumor—benign, borderline, and malignant subclasses, and sarcoma of the breast.

Breast cancer has been linked with a variety of biomarkers that have included the altered expression of p53, ER, PR, cell cycle proteins, B72.3, α-lactalbumin, milk fat globule, mammaglobin, maspin and HER2. However, not all breast cancers exhibit the altered expression of all of these biomarkers simultaneously, or to the same levels. Expression status of csPCNA and any of the other prognostic/diagnostic factors Ki67, p53, ER, PR, B72.3, α-lactalbumin, milk fat globule, mammaglobin, maspin and HER2 can also be performed. csPCNAab or commercially available primary antibodies to the other biomarkers, and the appropriate secondary antibodies to the others are used to evaluate correlation of csPCNA expression to other biomarkers for breast cancer. Monoclonal antibodies to csPCNA isoform are also used to detect and diagnose breast cancer tissue. Antigen-antibody binding conditions are adjusted if necessary to obtain optimal sensitivity.

Example 4C

Statistical Methods to Determine Sensitivity and Specificity of esPCNAab

Analysis of immunohistochemical (IHC) data is performed initially using the statistical approach (see S. C. Chuah et al. 2005, *Pathology* 37(2): pp., 169-171) for calculating the sensitivity and specificity of csPCNAab for detecting malignant breast cells in tissue specimens. In addition to these characteristics of csPCNAab, the positive (PPV) and negative (NPV) predictive values of using csPCNAab to distinguish malignant and non-malignant breast cells from one another, are determined using the following formulas. [Sensitivity=a/(a+c); Specificity=d/(b+c); PPV=[a/(a+b)]× 100; and NPV=[d/(c+d)]×100; where a=true positives, b=false positives, c=false negatives, and d=true negatives.] True/False positive and true/false negative staining of individual specimens are verified by pathologists during visual inspection of the stained tissue sections. The IHC data is also analyzed initially by the Chi-square test and the analysis is performed (see H. Brustmann, 2005, *Gynecologic Oncology* 98:396-402) on the data obtained using the IHC grading system described herein. The data is subjected to a univariate analysis, and the ability of csPCNAabs to distinguish between malignant and non-malignant breast specimens is evaluated. The data obtained with normal breast tissue specimens and benign breast lesions are analyzed using GraphPad Prism 4 and StatMate statistical analysis software (GraphPad, San Diego, Calif.), in order to quantify the ability of csPCNAab to selectively and specifically identify malignant breast cells in patient tissue specimens. csPCNAab should provide a selectivity of ≥90% and a confidence level of >95%, when the antibody is used to identify the presence of malignant breast cells in human breast biopsy material. csPCNAab reacts strongly even with tissue specimens classified as stage I disease. Different subcategories of breast cancer lesions are also evaluated by csPCNAabs disclosed herein.

Figure 13:
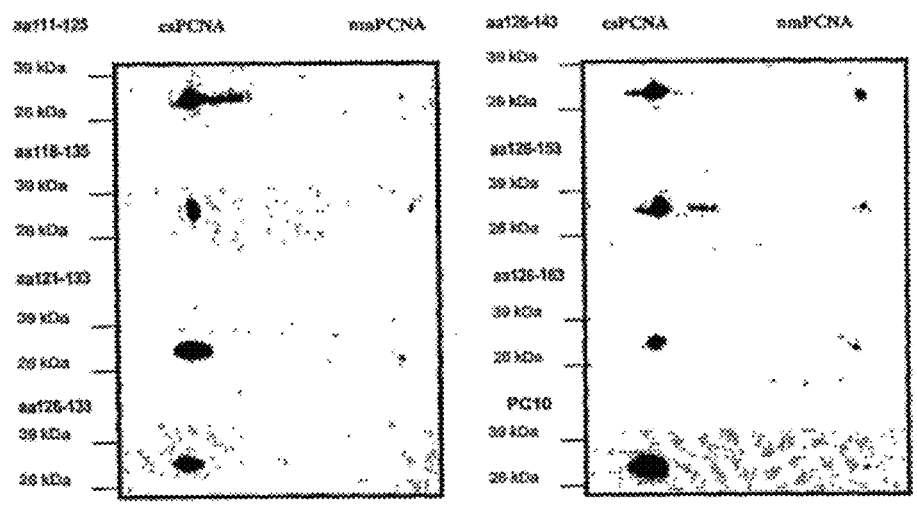
FIG. 13 shows that csPCNAab antibody specifically recognizes csPCNA. 60 μg of MCF7 cell extract were subjected to 2D-PAGE and Western blot analyses. The rabbit polyclonal antibodies prepared against the different PCNA peptide fragments and the commercially available PC10 antibody were each used at a dilution of 1:1000 in the Western blot analysis. The csPCNA isoform migrates to the acidic region of the gel which is oriented to the left side in the presented gel panels, while the nmPCNA isoform resolves to the basic region of the gel which is oriented to the right side of each gel panel. These gels are representative of at least three different experiments.

Example 5 csPCNA-Specific Peptide Design and Development of an Antibody Directed Specifically Against csPCNA Epitope mapping of commercially available antibodies for PCNA indicated that the majority of the antibodies bind within a 40-amino acid (aa) stretch in approximately the middle of the PCNA protein (aa85-125). This region represents an immuno-dominant domain within the PCNA polypeptide. Rabbit polyclonal antibodies were prepared by a commercial vendor (Zymed Inc, San Francisco, Calif.) to the peptide fragments of PCNA that included an interconnector domain (aa118-135) (Table 1), that facilitates PCNA's protein-protein interactions Each peptide was coupled to Keyhole Limpet Hemacyanin (KLH) through four cysteines residues added to the amino terminal portion of each peptide. 100 µg of each KLH conjugated peptide fragment was resuspended in complete Freund's adjuvant, and injected at multiple sites subcutaneously into 2 female New Zealand White rabbits/peptide. The rabbits were rested for one month prior to boosting the animals with a second 100 µg dose of the KLH coupled antigen in incomplete adjuvant. Antibody titer to the antigen was determined by ELISA assay approximately 10-14 days post-immunization, and after an additional 14 day rest period, the animals received a second boost of KLH coupled antigen. 12 days later, 25 ml of antisera was collected from each rabbit and stored at −20° C. The antisera was dialyzed against two changes of 20 mM phosphate buffered saline, pH 7.0, and loaded onto a protein G Sepharose column pre-equilibrated with the same buffered saline. One ml fractions eluting from the column were collected into 0.25 ml of 0.25M Tris-HCl pH 8.0. Fractions containing antibody were combined, dialyzed and stored at 4° C., until used in various assays. Western blot analysis was performed to evaluate each antibody's ability to specifically recognize csPCNA. A MCF7 breast cancer cell extract was resolved by 2D-PAGE. Western blot analysis of the resolved polypeptides was then performed using either different polyclonal antibodies or the commercial PC10 antibody (FIG. 13). PC10 antibody, like all commercially available antibodies to PCNA, recognizes both the basic isoform of PCNA (nmPCNA) found in non-malignant cells, and the acidic isoform of PCNA (csPCNA) found exclusively in breast cancer cells. Comparative analysis of all of the antibodies shows the ability of only one of the antibodies, the one prepared against PCNA peptide aa126-133, to only recognize csPCNA in 2D-PAGE Western blot analysis of cancer cell extracts. Data show that antibody raised against the whole interconnector domain (aa118-135) recognizes both nmPCNA and csPCNA. Also, antibody raised against PCNA aa121-133 binds both nmPCNA and csPCNA. The data also suggested that a csPCNA antigenic site lies somewhere between PCNA aa122-142. The antibody developed against PCNA aa126-133, (antibody that specifically recognizes csPCNA), has been designated as csPCNAab. In addition, peptide #126-133 has been used to successfully raise csPCNA specific antibody in four additional New Zealand white rabbits, and in 2 different strains of mice.

TABLE 1

PCNA peptide sequences used to generate rabbit polyclonal antibodies. (The peptides used are underlined).

PCNA Sequence 111-125

LVFEAPNQEK VSDYEMKLMD LDVEQLGIPEQEYSCVVKMP
SGEFARICRD LSHIGDAVVI SCAKDGVKFS ASGELGNGNI
KLSQTSNVDK EEEAVTIEMN

PCNA Sequence 118-135

LVFEAPNQEK VSDYEMKLMD LDVEQLGIPEQEYSCVVKMP
SGEFARICRD LSHIGDAVVI SCAKDGVKFS ASGELGNGNI
KLSQTSNVDK EEEAVTIEMN

PCNA Sequence 121-133

LVFEAPNQEK VSDYEMKLMD LDVEQLGIPEQEYSCVVKMP
SGEFARICRD LSHIGDAVVI SCAKDGVKFS ASGELGNGNI
KLSQTSNVDK EEEAVTIEMN

PCNA Sequence 126-133

LVFEAPNQEK VSDYEMKLMD LDVEQLGIPEQEYSCVVKMP
SGEFARICRD LSHIGDAVVI SCAKDGVKFS ASGELGNGNI
KLSQTSNVDK EEEAVTIEMN

PCNA Sequence 126-143

LVFEAPNQEK VSDYEMKLMD LDVEQLGIPEQEYSCVVKMP
SGEFARICRD LSHIGDAVVI SCAKDGVKFS ASGELGNGNI
KLSQTSNVDK EEEAVTIEMN

PCNA Sequence 126-153

LVFEAPNQEK VSDYEMKLMD LDVEQLGIPEQEYSCVVKMP
SGEFARICRD LSHIGDAVVI SCAKDGVKFS ASGELGNGNI
KLSQTSNVDK EEEAVTIEMN

PCNA Sequence 126-163

LVFEAPNQEK VSDYEMKLMD LDVEQLGIPEQEYSCVVKMP
SGEFARICRD LSHIGDAVVI SCAKDGVKFS ASGELGNGNI
KLSQTSNVDK EEEAVTIEMN

Example 5A

Specificity of the Antibody for csPCNA

This example demonstrates the specificity of the antibodies for csPCNA. A direct ELISA assay was performed in which the antigenic peptide and purified csPCNA, were allowed to compete with one another as targets for binding by the anti-PCNA antibody ("Ab126 antibody"). If the antibody were specific for csPCNA, then at a sufficient concentration, the peptide used to raise this antibody would be expected to effectively compete with the purified csPCNA for binding to the Ab126 antibody placed in the assay.

The experiment was performed by immobilizing 0.1 µg of the recombinant PCNA to the ELISA plate in coupling buffer (carbonate buffer, pH 9.6), followed by incubation with 1% bovine serum albumin in coupling buffer for 1 hour to block residual binding sites remaining in each well. Then a range of concentrations (0.024 ng/well-2400 ng/well) of the antigenic peptide (UMPB6—equivalent to PCNA amino acids 126-133) was mixed on ice with the Ab126 antibody and placed in each well for an hour at room temperature with shaking. This primary antibody was removed by washing with PBS-0.05% Tween 20 and anti-rabbit IgG secondary antibody conjugated to Alkaline phosphatase was added to each well. The wells were washed with PBS, and 100 µl of para-nitrophenolphosphate (1 mg/ml) in reaction buffer, was incubated for 20 minutes to hydrolyze the substrate, prior to reading the optical density of the reaction mixture at a wavelength of 405 nm.

The results shown in FIG. 15A demonstrate the ability of the peptide to inhibit the binding of the Ab126 antibody to the csPCNA immobilized on the ELISA plate as a function of increasing peptide concentration, with an apparent IC50 of slightly over 0.1 µg/ml. This data demonstrates the specificity of the Ab126 antibody for the csPCNA isoform of the protein.

Example 5B

Specificity of AB126 Antibody in a Sandwich ELISA

This example demonstrates the specificity of antibodies disclosed herein to csPCNA in a sandwich ELISA. A sandwich ELISA was performed in which either the csPCNA specific Ab126 antibody (1 µg/well) or the non-specific PCNA antibody C20 (1 µg/well) was immobilized to the ELISA plate, and used to capture the recombinant PCNA used in the assay. Residual binding sites on the ELISA plate were blocked with BSA, and recombinant PCNA was incubated with the immobilized capture antibody in the presence of a range of concentrations of competing peptide (UMPB6—(0.024 ng/well-2400 ng/well)). After washing off unbound PCNA, the bound protein was detected with the C20 antibody in the first case, and with Ab126 in the second case. These detection antibodies were added to each well of the ELISA plate. The appropriate alkaline phosphatase conjugated secondary anti-rabbit or anti-goat IgG antibody was incubated with the bound antibody in each of the ELISA plate wells, and after washing away non-specifically bound antibody with PBS-0.05% Tween 20, the amount of detection antibody bound to the captured PCNA was determined by incubating the secondary antibody remaining in each well with 1 mg/ml of p-nitrophenolphosphate for 30 minutes.

The results shown in FIG. 15B, indicate that when a specific capture antibody (Ab126—diamonds) was used to capture the csPCNA isoform present in the recombinant PCNA added to the assay, the UMPB6 peptide was efficient at competing for the capture antibody; with an apparent IC50 in this type of assay of slightly over 1 µg/well. In contrast, UMPB6 had no detectable effect on the ability of the C20 antibody (pink squares) to capture the recombinant PCNA. This may be due to the fact the binding site of the non-isoform specific C20 antibody does not recognize the UMPB6 peptide as its targeted epitope. The overall difference in the amount of binding between the two antibodies may arise from differences in the affinity of the two antibodies for the recombinant PCNA protein, or is the result of a mixture of PCNA molecules in the recombinant protein—including csPCNA and non-csPCNA isoforms of the recombinant protein.

Example 5C

Sensitivity of the ELISA for csPCNA

This example demonstrates the sensitivity of csPCNA specific antibodies disclosed herein. The sensitivity of the ELISA assay was determined by measuring the ability of the assay to detect csPCNA over a range of concentrations. The sandwich ELISA was performed as outlined herein using the non-specific anti-PCNA antibody (C20 antibody) to capture the csPCNA isoform present in the purified recombinant PCNA used in the assay. The bound antibody was visualized specifically using the Ab126 antibody to detect the presence of csPCNA bound to the C20 antibody. Anti-rabbit IgG conjugated to alkaline phosphatase was used to identify the presence of Ab126 antibody bound to the captured csPCNA. As illustrated in FIG. 15C, the assay detects csPCNA over a range of concentrations spanning from 3-200 ng/well.

Example 5D

Detection of csPCNA in a Cancer Cell Extract

Figure 16:
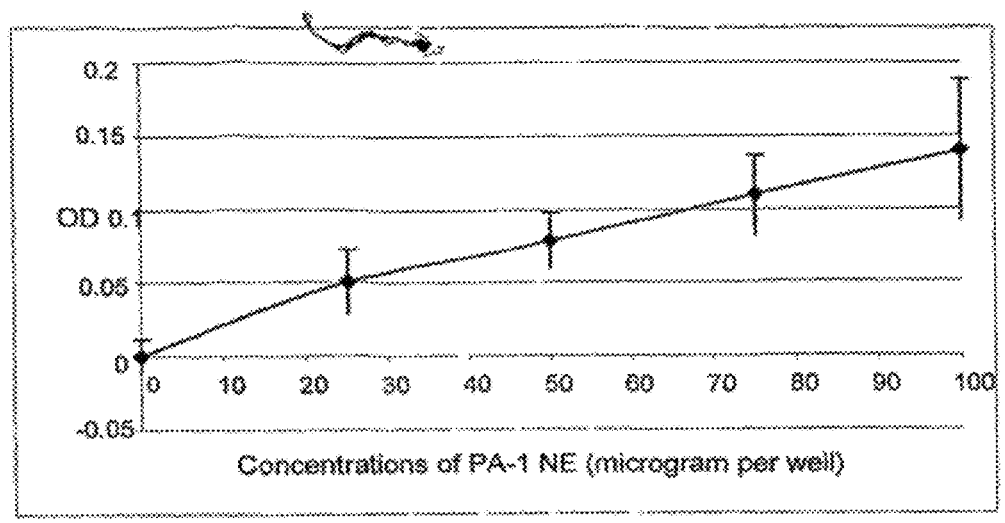
FIG. 16 shows the detection of csPCNA isoform in a cancer cell extract.

This example demonstrates the ability of csPCNA specific antibody to detect the csPCNA isoform in a cancer cell extract. Ovarian cancer cells (including the PA-1 cell line) have been shown to express the csPCNA isoform. Using the sandwich ELISA described herein, increasing concentrations of a nuclear extract prepared from PA-1 cells were incubated and it was demonstrated that over a range of concentrations of nuclear extract spanning from 0-100 µg/well, the presence of csPCNA in the extract was detected. Detection of csPCNA, as shown in FIG. 16, was linear over the range of protein examined using the Ab126 antibody. PCNA expressed by the PA-1 cells was captured by the C20 antibody immobilized to the ELISA well.

Example 6 csPCNA Participates in DNA Replication and Interacts with POL 6

PCNA is a functioning component of the synthesome. In addition, the functional response of the synthesome to DNA pol α and δ inhibitors, pol α antibody, and the requirement for PCNA suggested that in vitro replication activity of the synthesome is mediated by both pols α and δ. To now determine whether csPCNA actually plays a role in breast cancer cell DNA replication and functions with its pol δ, DNA pol δ and in vitro SV40 DNA replication assays were performed in the presence and absence of csPCNAab using a MCF7 cell extract (Table 2). It was observed that csPCNAab inhibited both DNA pol 6 and in vitro SV40 DNA replication activity in the breast cancer cell extract. Bovine serum albumin (BSA) was added to control reactions and no inhibition was noted. These results show that csPCNA can actively participate in breast cancer cell DNA replication and readily function with DNA pol δ.

TABLE 2

Effect of increasing csPCNAab concentrations on in vitro SV40 DNA replication and DNA pol δ activities.

| csPCNAab | % Inhibition | |
| --- | --- | --- |
| Concentration (µg) | In vitro SV40 DNA Replication* | DNA Pol δ** |
| 0.1 | 29 | N/D# |
| 2.0 | 40 | 34 |
| 5.0 | N/D | 57 |
| 10.0 | 48 | 63 |

Prior to reaction initiation, synthesome fraction was incubated with increasing concentrations of csPCNAab for 1 hour at 4°C. Data represent the mean of 3 independent experiments.
Not Determined.
*SV40 DNA replication assay and DNA polymerase assay was performed according to published procedures (Malkas, L. H. et al., (1990), Biochem. 29: 6362-6374; Waleed et al., (2004), Biochemical Pharmacology 68: 11-21; and Han et al., (2000), Biochemical Pharmacology 60: 403-411).

The results demonstrate that csPCNA specific antibodies can selectively inhibit DNA replication and serve as a therapeutic tool to inhibit cancer cell replication. csPCNA specific antibodies also affect protein-protein interactions of the csPCNA isoform and thereby affecting cancer cell replication pathways.

Example 7

Autoantibodies to csPCNA

This example demonstrates the use of auto-antibodies to csPCNA isoform as a tool to detect circulating csPCNA isoforms and to diagnose early and late stage cancers.

The experimental design involves coating an enzyme linked immunosorbent assay (ELISA) plate with a recombinant PCNA containing the csPCNA isoform, blocking the ELISA wells with BSA, and incubating the coated wells with human serum from the stage IV patients. Patients were divided into two groups. One group contained individuals who survived for less than 200 days following enrollment in the trial, while the other group survived for greater than 1300 days following enrollment. The wells were then washed with PBS, and incubated with anti-human antibody conjugated to Horse Radish Peroxidase (HRP). If circulating antibody against PCNA were present in the patient sera specimens, these anti-PCNA antibodies would bind the PCNA bound to the plate, and be retained on the plate following the washing step. Anti-human secondary antibody would be expected to bind to the antibody in those wells containing patient sera expressing anti-PCNA antibodies. The presence of the anti-human antibody would be noted by the conversion of the p-nitrophenol phosphate substrate to a yellow product. The abundance of the product is determined by measuring its absorbance at 405 nm. The results indicated that one of the long-term survivors had a considerable amount of freely circulating anti-PCNA antibody, while a single short term survivor was making a small amount of this same type of antibody. One patient from each group had an undetectable level of anti-PCNA antibody that did not appear to correlate with either long or short term survival. FIG. 14 shows the raw data, the controls, and the experiments minus the background derived from the controls. The ELISA procedure for auto-antibodies is outlined herein. Briefly the ELISA plate is coated with 0.2 µg of PCNA and the volume is brought to 100 p. 1 with coupling Buffer (50 mM Carbonate buffer pH 9.6; 10 mM NaN3) and the plate is shaken for 2 hrs at 37° C. The concentration of PCNA is about 0.250 µg/µl. 200 µl Blocking Buffer (1×PBS, pH 7.4; 1% BSA; 0.05% Tween 20) is used to block the unbound sites for 1 hr at 37° C. Washing is done 3 times with a wash buffer (1×PBS, pH 7.4; 0.05% Tween 20). 50 µl of human serum (stage IV breast cancer patient) is added and incubated for 1 hr at 37° C. The initial serum is removed and replaced with 500 of fresh serum and is incubated for 1 hr at 37° C. The plate is then washed three times with wash buffer. After the washing, 100 µl 2° Ab Anti-Human AP (1:1000) is added and the plate is incubated for 1 hr. at 37° C. Washing is done 3 times with a wash buffer. To develop color, 100 µl of 1 mg/ml p-nitrophenol phosphate (pNPP) (in 10 mM diethanolamine, pH 9.0; 0.5 mM MgC12) is added and incubated for ~10-30 min at room temperature depending on degree of color development. The color development is stopped by adding 50 µl of 1% SDS and the absorbance is measured at 405 nm.

The absorbance units are correlated to the amount of auto-antibodies in the serum. Presence of auto-antibodies to csPCNA isoform indicates the presence of free circulating csPCNA isoform in the individual and therefore indicates the presence of malignant cells. The amount of circulating csPCNA isoform may vary depending upon the stage of cancer and cancer types.

Example 8

In Vivo Detection of Cancer Cells and Delivery of csPCNA Antibody to Tumor Cells The antibody, phage display antibody, or XPG-fragment interacting with csPCNA may be used to identify the location of a tumor within a subject or patient by adding a radioisotope label (e.g., F18) or fluorescent tag to the reagent and injecting the csPCNA specific reagent into the subject to allow the tumor cells to react with the labeled reagent (antibody, phage particle). The accumulation of the labeled reagent at a particular site within the subject is then monitored by a suitable device such as a CCD camera or PET scanner and the tumor is so located with the accumulation of labeled reagent.

Similarly, the antibody, phage display antibody, or XPG-fragment interacting with csPCNA is incorporated into a liposome delivery vesicle for delivery to the tumor. Delivery is achieved when the antibody, phage particle, or XPG-fragment incorporated into the liposome reacts with the csPCNA. Released agents into the cancer cell would interact with the csPCNA in the cancer cell and compete for cellular biochemical reactions involving csPCNA. These reactions are slowed or disrupted when the csPCNA binding partners interact with the competing csPCNA peptide, or remove the csPCNA from the cancer cell by forming a complex with the csPCNA, thus preventing csPCNA from interacting with its naturally intended binding partners (e.g., but not limited to DNA Polymerase delta, DNA repair proteins, the transcriptional machinery, and proteins involved in DNA recombination.)

The liposome may also be packed with a specific cocktail of traditional chemotherapeutic drugs used or being tested in the clinical setting to treat a variety of malignancies. Incorporations of the csPCNA specific antibodies, phage particles, or XPG-fragment or fragments of protein known to bind csPCNA (e.g., but not limited to p21 cip/waf1) would permit the therapeutic liposome to accumulate at the tumor cite and fuse with the tumor within and adjacent to the tumor. Because of the selectivity of the csPCNA reagents for csPCNA, these reagents will not disrupt nmPCNA-protein interactions and therefore spare non-malignant cells from the cell killing effects mediated by disrupting csPCNA protein specific interactions.

The liposomes may also be packed with specific immune system stimulatory molecules or agents capable of stimulating an immune response at the site of the tumor upon delivery of the stimulatory molecule to the tumor cells or cells at the tumor site. Tumor site specific delivery will be achieved by incorporation of the csPCNA specific antibodies, phage particles, XPG or other protein fragment into the surface of the liposome and allowing the liposome to react with the tumor cells and tumor environment following injection of these therapeutic liposomes into the subject having a tumor.

While the peptides, antibodies and uses thereof relating to csPCNA isoform have been described in detail, and with reference to specific embodiments thereof, it will be apparent to one with ordinary skill in the art that various changes and modifications can be made therein without departing from the spirit and scope thereof. All references cited herein are incorporated by reference in their entirety.

We claim:

1. An isolated antibody that specifically binds cancer specific proliferating cell nuclear antigen (csPCNA) isoform, wherein the antibody does not bind to non-malignant proliferating cell nuclear antigen (nmPCNA), and wherein the antibody binds to an epitope of csPCNA comprising an amino acid sequence selected from LGIPEQEY (SEQ ID NO: 1), QLGIPEQEY (SEQ ID NO: 9), LGIPEQEYSCVV (SEQ ID NO: 13), LGIPEQEYSCV (SEQ ID NO: 14), and LGIPEQEYSC (SEQ ID NO: 15).

2. The antibody of claim 1, wherein the csPCNA isoform comprises the amino acid sequence of SEQ ID NO: 3.

3. The antibody of claim 1, wherein the antibody binds to an epitope comprising an amino acid sequence within the csPCNA protein that binds to Xeroderma pigmentosum Group G (XPG) protein.

4. The antibody of claim 1, wherein the antibody is a monoclonal antibody.

5. The antibody of claim 1, wherein the antibody is a chimeric antibody.

6. The antibody of claim 1, wherein the antibody is a recombinant antibody.

7. The antibody of claim 1, wherein the antibody is a single chain antibody.

8. The antibody of claim 1, wherein the antibody is an antibody fragment selected from Fab, Fab', or F(ab')2.

9. The antibody of claim 1, wherein the antibody is associated with a detectable agent.

10. The antibody of claim 1, wherein the detectable agent is selected from a fluorescent label, radio label, chromatogenic label, and an enzymatic label.

11. A composition comprising an isolated and substantially purified antibody that specifically binds to an epitope of cancer specific proliferating cell nuclear antigen (csPCNA), wherein the epitope comprises an amino acid sequence of LeuGlyIleProGluGlnGluTyr (SEQ ID NO: 1) and the epitope is not available for binding to the antibody on non-malignant proliferating cell nuclear antigen (nmPCNA).

12. An immunoassay kit for detecting the csPCNA isoform of PCNA comprising:
the antibody preparation of claim 1 that specifically binds only to a cancer specific proliferating cell nuclear antigen (csPCNA) isoform and not to the normal proliferating cell nuclear antigen (nmPCNA) isoform, and wherein the antibody binds to an epitope of csPCNA comprising an amino acid sequence selected from LGIPEQEY (SEQ ID NO: 1), QLGIPEQEY (SEQ ID NO: 9), LGIPEQEYSCVV (SEQ ID NO: 13), LGIPEQEYSCV (SEQ ID NO: 14), and LGIPEQEYSC (SEQ ID NO: 15), whereby the antibodies and csPCNA form a complex; and reagents for detecting the complex.

13. The immunoassay kit of claim 12 comprising a peptide of amino acid sequence selected from LGIPEQEY (SEQ ID NO: 1), QLGIPEQEY (SEQ ID NO: 9), LGIPEQEYSCVV (SEQ ID NO: 13), LGIPEQEYSCV (SEQ ID NO: 14), and LGIPEQEYSC (SEQ ID NO: 15), wherein the peptide is used as a positive control.

14. A method for the detection of a cancer specific proliferating cell nuclear antigen (csPCNA) isoform in a biological sample comprising:
contacting the biological sample with the antibody of claim 1 that specifically binds cancer specific proliferating cell nuclear antigen (csPCNA) isoform but not a nonmalignant proliferating cell nuclear antigen (nmPCNA);
providing conditions for the antibody binding; and
detecting the binding of the antibody with the csPCNA isoform.

15. The method of claim 14, wherein the biological sample is a bodily fluid.

16. The method of claim 15, wherein the bodily fluid is selected from the group consisting of blood, plasma, lymph, serum, pleural fluid, spinal fluid, saliva, sputum, urine, gastric juice, pancreatic juice, ascites fluid, synovial fluid, milk, and semen.

17. The method of claim 14, wherein the biological sample is a tissue sample.

18. The method of claim 17, wherein the tissue is selected from breast, prostrate, lung, colon, epithelial, connective, cervical, esophageal, brain, thymus, thyroid, pancreas, testis, ovary, intestine, bladder, stomach, soft tissue sarcomas, osteosarcoma, leukemia, lymphoma, carcinoma, adenocarcinoma, placenta, fibrous, germ cell tissue, and extracts thereof.

19. The method of claim 14, wherein the antibody detection is performed in vivo.

20. The method of claim 14, wherein the antibody detection is performed by providing a labeled secondary antibody.

21. The method of claim 14, wherein the antibody that specifically binds cancer specific proliferating cell nuclear antigen (csPCNA) isoform is labeled.

22. The method of claim 14, wherein the detection of csPCNA isoform is performed using a mass spectrometric analysis.

23. The method of claim 14, wherein the detection of csPCNA isoform is performed using an enzyme linked immunosorbent assay.

24. The method of claim 14, wherein the detection of csPCNA isoform is performed using an immunohistochemical method.

25. A method to diagnose malignancy of a tissue or cell, comprising:
detecting csPCNA in a biological sample obtained from an animal by an antibody that specifically binds cancer specific proliferating cell nuclear antigen (csPCNA) isoform but does not bind to nonmalignant cancer specific proliferating cell nuclear antigen (nmPCNA) and wherein the antibody binds to an epitope of csPCNA comprising an amino acid sequence selected from LGIPEQEY (SEQ ID NO: 1), QLGIPEQEY (SEQ ID NO: 9), LGIPEQEYSCVV (SEQ ID NO: 13), LGIPEQEYSCV (SEQ ID NO: 14), and LGIPEQEYSC (SEQ ID NO: 15); and
diagnosing malignancy based on the detection of csPCNA in the biological sample.

26. The method of claim 25, wherein the biological sample is a biological tissue or a fluid.

27. A method for producing antibodies specific to a cancer specific proliferating cell nuclear antigen (csPCNA) isoform comprising:
administering to an antibody generation source an immunogenic amount of a peptide representing an epitope that is exposed only on the csPCNA isoform, but not on a non-malignant isoform (nmPCNA), wherein the peptide is selected from contiguous or noncontiguous amino acid residues on the region of csPCNA that interacts with a Xeroderma pigmentosum group G (XPG) protein, and wherein the peptide comprises an amino acid sequence selected from LGIPEQEY (SEQ ID NO: 1), CGGGLGIPEQEY (SEQ ID NO.: 2), QLGIPEQEY (SEQ ID NO: 9), LGIPEQEYSCVV (SEQ ID NO: 13), LGIPEQEYSCV (SEQ ID NO: 14), and LGIPEQEYSC (SEQ ID NO: 15);
providing conditions for antibody generation; and
isolating and purifying the antibodies that specifically binds cancer specific proliferating cell nuclear antigen (csPCNA) isoform, wherein the antibody does not bind to non-malignant proliferating cell nuclear antigen (nmPCNA), and wherein the antibody binds to an epitope of csPCNA comprising an amino acid sequence selected from LGIPEQEY (SEQ ID NO: 1), QLGIPEQEY (SEQ ID NO: 9), LGIPEQEYSCVV (SEQ ID NO: 13), LGIPEQEYSCV (SEQ ID NO: 14), and LGIPEQEYSC (SEQ ID NO: 15).

28. The method of claim 27, wherein the antibodies are isolated and purified from hybridoma cells.

29. The method of claim 27, wherein the peptide is attached to a carrier protein.

30. The method of claim 29, wherein the carrier protein is keyhole limpet hemocyanin (KLH).

31. A method to identify the location of a tumor in vivo, the method comprising:
    administering a cancer specific proliferating cell nuclear antigen (csPCNA) isoform specific antibody of claim 1 that binds csPCNA but not to a nonmalignanc proliferating cell nuclear antigen (nmPCNA), wherein the antibody is labeled with a radioactive or fluorescent tag; and
    determining the location of the tumor by detecting the accumulation of the labeled csPCNA-specific antibody at the tumor site.

32. A method of identifying an anti-cancer agent comprising:
    contacting a population of cancer cells with an agent;
    measuring the levels of a cancer specific proliferating cell nuclear antigen (csPCNA) isoform by assaying the binding of the csPCNA-specific antibody of claim 1 to the csPCNA isoform; and
    determining that the agent is an anticancer agent if the levels of csPCNA isoform in the cancer cells contacted with the agent is less than the levels of csPCNA isoform in cancer cells not contacted with the agent.

33. The method of claim 32, wherein the agent is a small molecule.

34. The method of claim 32, wherein the population of cancer cells is selected from the group consisting of a cancer cell line, xenograft and an orthotopic model system of cancer.

35. The method of claim 32, wherein the determining step further comprises measuring the levels of non-malignant PCNA isoform in normal cells contacted with the agent and in normal cells not contacted with the agent.

36. The method of claim 32, wherein the identification of the anti-cancer agent is performed in a high-throughput system.

37. The immunoassay kit of claim 12 comprising a preparation of csPCNA isoform comprising amino acid sequence of SEQ ID NO: 3, wherein the csPCNA isoform is used as a positive control.

38. A method of monitoring the remission status of an individual, the method comprising:
    detecting the presence of proliferating cell nuclear antigen (csPCNA) isoform in the individual prior to and after cancer therapy, utilizing the antibody of claim 1; and
    determining the remission status of the individual by comparing the levels of circulating csPCNA isoform prior to and after cancer therapy; wherein a decreased level of csPCNA indicates that the individual is in remission.

39. The method of claim 38, wherein the csPCNA isoform is detected by an enzyme linked immunosorbent assay.

40. The method of claim 25, wherein the animal is a human subject.

41. The method of claim 31, further comprising the step of measuring tumor progression after administration of the csPCNA isoform specific antibody.

* * * * *